(12) United States Patent
Maris et al.

(10) Patent No.: US 6,208,421 B1
(45) Date of Patent: Mar. 27, 2001

(54) OPTICAL STRESS GENERATOR AND DETECTOR

(75) Inventors: Humphrey J. Maris, Barrington, RI (US); Robert J Stoner, Duxbury, MA (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 09/512,141

(22) Filed: Feb. 23, 2000

Related U.S. Application Data

(62) Division of application No. 09/382,251, filed on Aug. 24, 1999, which is a division of application No. 08/954,347, filed on Oct. 17, 1997, now Pat. No. 5,959,735, which is a division of application No. 08/689,287, filed on Aug. 6, 1996, now Pat. No. 5,748,318
(60) Provisional application No. 60/010,543, filed on Jan. 23, 1996.

(51) Int. Cl.$^7$ .................... G01N 21/00; G01B 11/06

(52) U.S. Cl. ............................ 356/432; 356/381

(58) Field of Search ........................ 356/432, 381; 250/201.2, 201.4; 364/562, 563, 578

(56) References Cited

U.S. PATENT DOCUMENTS

| 3,950,987 | 4/1976 | Slezinger et al. ............. 73/141 A |
| 4,484,820 | 11/1984 | Rosencwaig .................. 374/6 |
| 4,522,510 | 6/1985 | Rosencwaig et al. ........... 374/7 |
| 4,579,463 | 4/1986 | Rosencwaig et al. ........... 374/57 |
| 4,632,561 | 12/1986 | Rosencwaig et al. ........... 356/432 |

(List continued on next page.)

FOREIGN PATENT DOCUMENTS 7-22482 * 1/1995 (JP).

OTHER PUBLICATIONS

W. Lee Smith et al. "Ion imolant monitoring with thermal wave technology". Appl. Phys.Lett., vol. 47, No. 6, Sep. 15, 1985. p.584–586.
J. Opsal et al. "Thermal and plasma wave depth profiling in silicon". Appl. Phys. Lett. vol. 47 No. 5, Sep. 1, 1985. p.498–500.
A. Rosencwaig et al. "Thin–film thickness measurements with thermal waves". Appl. Phys. Lett., vol. 43 No. 2, Jul. 15, 1983. p.166–168.
A. Rosencwaig et al. "Detection of thermal waves through optical reflectance". Appl. Phys. Lett., vol. 46 No. 11, Jun. 1, 1985. p.1013–1015.
A. Elci et al. "Physics of Ultrafast Phenomena in Solid State Plasmas". Solid–State Electronics, vol. 21, 1978, p.151–158.

(List continued on next page.)

Primary Examiner—Frank G. Font
Assistant Examiner—Zandra Smith
(74) Attorney, Agent, or Firm—Ohlandt, Greeley, Ruggiero & Perle, L.L.P.

(57) ABSTRACT

Disclosed is a system for the characterization of thin films and interfaces between thin films through measurements of their mechanical and thermal properties. In the system light is absorbed in a thin film or in a structure made up of several thin films, and the change in optical transmission or reflection is measured and analyzed. The change in reflection or transmission is used to give information about the ultrasonic waves that are produced in the structure. The information that is obtained from the use of the measurement methods and apparatus of this invention can include: (a) a determination of the thickness of thin films with a speed and accuracy that is improved compared to earlier methods; (b) a determination of the thermal, elastic, and optical properties of thin films; (c) a determination of the stress in thin films; and (d) a characterization of the properties of interfaces, including the presence of roughness and defects.

7 Claims, 16 Drawing Sheets

U.S. PATENT DOCUMENTS

| | | | |
|---|---|---|---|
| 4,636,088 | 1/1987 | Rosencwaig et al. | 374/5 |
| 4,679,946 | 7/1987 | Rosencwaig et al. | 374/5 |
| 4,710,030 * | 12/1987 | Tauc et al. | 356/432 |
| 4,750,822 | 6/1988 | Rosencwaig et al. | 356/445 |
| 4,795,260 | 1/1989 | Schuur et al. | 356/400 |
| 4,844,617 | 7/1989 | Kelderman | 356/372 |
| 4,854,710 | 8/1989 | Opsal et al. | 356/432 |
| 4,952,063 | 8/1990 | Opsal et al. | 356/432 |
| 4,999,014 | 3/1991 | Gold et al. | 356/382 |
| 5,042,951 | 8/1991 | Gold et al. | 356/369 |
| 5,042,952 | 8/1991 | Opsal et al. | 356/432 |
| 5,074,669 | 12/1991 | Opsal | 356/445 |
| 5,083,869 | 1/1992 | Nakata et al. | 356/432 |
| 5,131,752 | 7/1992 | Yu et al. | 356/369 |
| 5,227,912 | 7/1993 | Ho et al. | 359/578 |
| 5,379,109 | 1/1995 | Gaskill et al. | 356/445 |
| 5,481,475 | 1/1996 | Young | 364/578 |
| 5,546,811 | 8/1996 | Rogers et al. | 73/800 |
| 5,574,562 | 11/1996 | Fishman et al. | 356/432 |
| 5,585,921 | 12/1996 | Pepper et al. | 356/357 |

OTHER PUBLICATIONS

D.H. Auston et al. "Picosecond Spectroscopy of Semiconductors". Solid–State Electronics, vol. 21, 1978, p.147–150.

D. H. Auston et al. "Picosecond Ellipsometry of Transient Electron–Hole Plasmas in Germanium". Physical Review Letters, vol. 32 No. 20. May 20, 1974 p.1120–1123.

R.J. Stoner et al. "Kapitza conductance and heat flow between solids at temperatures from 50 to 300K". Physical Review B, vol. 48, No. 22, Dec. 1, 1993 p.16 373–16 387.

R.J. Stoner et al. "Measurements of the Kapitza Conductance between Diamond and Several Metals". Physical Review Letters, vol. 68 No. 10, Mar. 9, 1992 p.1563–1566.

S. Sumie et al. "A New Method of Photothermal Displacement Measurement by Laser Interferometric Probe". Jpn. J. Appl. Phys. vol. 31 Pt. 1, No. 11, 1992 p.3575–3583.

S. Sumie et al. J.Appl. Phys. 76(10), Nov. 15, 1994 p.5681–5689.

F.E. Doany et al. "Carrier lifetime versus ion–implantation dose in silicon on sapphire". Appl. Phys. Lett. 50(8), Feb. 23, 1987 p.460–462.

D.A. Young et al. "Heat Flow in Glasses on a Picosecond Timescale". Dept. of Engineering, Brown University, Providence, RI. 1986. p.49–51.

H.T. Grahn et al., "Time–resolved study of vibrations of a Ge:H/aSi:H multilayers", Phys. Review B, vol. 38, No. 9, Sep. 15, 1988.

H.T. Grahn et al.,"Sound velocity and index of refraction of AIAs measured by picosecond ultrasonics", Appl. Phys. Lett. 53, Nov. 21, 1988.

H.T. Grahn et al., "Elastic properties of silicon oxynitride films determined by picosecond acoustics", App. Phys. Lett. 53, Dec. 5, 1988.

H.T. Grahn et al., "Icosecond Ultrasonics", IEEE, vol. 25, #12, Dec. 1989.

H.N. Lin, et al., "Nondestructive Testing of Microstructures by Picosecond Ultrasonics", Journal of Non–Destructive Evaluation, vol. 9 No. 4, 1990.

G.J. Flechtner et al., "Measurements of atomic sodium in flames by asynchronous optical sampling: theory and experiment", Applied Optics, vol. 31, No. 15, May 20, 1992.

O.B. Wright, et al."Characterization Of Transparent And Opaque Thin Films Using Laser Picosecond Ultrasonics", Nondestr. Test Eval. vol. 7, pp. 149–163.

O.B. Wright, "Thickness and sound velocity measurement in thin transparent films with laser picosecnd acoustics", Journal of Applied Physics, vol. 71, #4, Feb. 15, 1992.

O.B. Wright, et al., "High Resolution Laser Picosecond Acoustics In Thin Films", Symp. on Physical Acoustics. Belgium, 1990.

O.B. Wright et al., "Laser Picosecond Acoustics in Various Types of Thin Film", Japanese Journal of Applied Physics, vol. 31 (1992).

C.A. Paddock et al., "Transient thermoreflectance from thin metal films", J. Appl. Phys. 60, Jul. 1, 1986.

D.M. Pennington et al., "Direct Measurement of the Thermal Expansion of a Surface Using Transient Gratings", Optical Society.

K. A. Svinarich et al., "Picosecond Acoustic Pulse Reflection From A Metal–Metal Interface", Dept. of Physics, Wayne State University.

G.L. Eesley et al., "Generation and detecting of picosecond acoustic pulses in thin metal films", Appl. Phys. Lett. 50, Mar. 23, 1987.

B.M. Clemens et al., "Relationship between Interfacial Strain and the Elastic Response of Multilayer Metal Films", Physical Review Letter, vol. 61, No. 20, Nov. 14, 1988.

G. Tas et al., "Picosecond Ultrasonic Investigation of Thin Interfacial Layers Between Films and a Substrate", IBM T. J. Watson Research Center.

H.J. Maris et al., "Studies of High–Frequency Acoustic Phonons Using Picosecond Optical Techniques", Dept. of Physics, Brown University.

C. Thomsen et al., "Picosecond Acoustics As A Non–Destructive Tool For the Characterization Of Very Thin Films", Thin Solid Films 154 (1987).

P.A. Elzinga et al., "Pump/probe method for fast analysis of visible spectral signatures utilizing asynchronous optical sampling", Applied Optics, vol. 26, No. 19, Oct. 1, 1987.

R. J. Kneisler et al., "Asynchronous optical sampling: a new combustion diagnostic for potential use in turbulent, high–ressure flames", 1989 Optics Letters, vol. 14, No. 5.

C. Thomsen et al., "Surface generation and detection of phonons by picosecond light pulses", Physical Review B, vol. 34, No. 6, Sep. 15, 1986.

G. Tas et al., "Noninvasive picosecond ultrasonic detection of ultrathin interfacial layers: $CF_x$ at the Al/Si interface", Appl. Phys. Lett. 61, Oct. 12, 1992.

H. N. Lin et al., "Study of vibrational modes of gold nanostructures by picosecond ultrasonics", J. Appl. Phys. 73, Jan. 1, 1993.

H.J. Maris et al., Picosecond Optics Studies of Vibrational and Mechanical Properties of Nanostructures, AMD–vol. 140, Acousto–Optics and Acoustic Microscopy, ASME 1992.

C.J. Morath et al., "Picosecond optical studies of amorphous diamond and diamondlike carbon: Thermal conductivity and longitudinal sound velocity", J. Appl. Phys. 76, Sep. 1, 1994.

H.N. Lin et al., "Nondestructive detection of titanium disilicide phase transformation by picosecond ultrasonics", IBM T. J. Watson Research Center.

H.T. Grahn et al., "Picosecond Photoinduced Electronic and Acoustic Effects In a Si:H Based Multilayer Structures", Journal of Non–Crystalline Solids 97&98, 1987.

H.N. Lin et al., "Phonon Attenuation and Velocity Measurements in Transparent Materials by Picosecond Acoustic Interferometry", Journal of Applied Physics, vol. 69, Apr. 1, 1990.

T.C. Zhu et al., Attenuation of longitudinal–acoustic phonons in amorphous $SiO_2$ at frequencies up to 440 GHz, Physical Review B, vol. 44, #9, Sep. 1, 1991.

H.N. Lin et al., Ultrasonic Experiments At Ultra–High Frequency With Picosecond Time–Resolution, IEEE Ultrasonics Symp. 90.

H.N. Lin et al., "Detection of Titanium Silicide Formation and Phase Transportation by Picosecond Ultrasonics," MRS.

G. Tas et al., "Detection Of Thin Interfacial Layers By Picosecond Ultrasonics", Mat. Res. Soc. Symp. Proc. vol. 259, 1992.

* cited by examiner

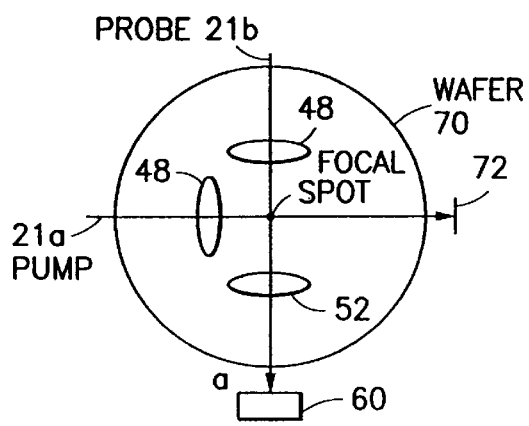
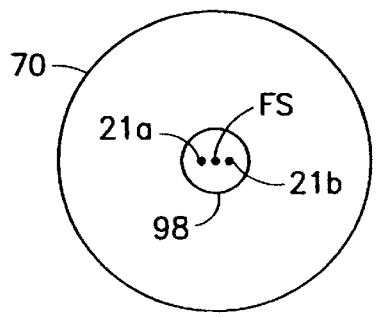
FIG. 3a  FIG. 3b
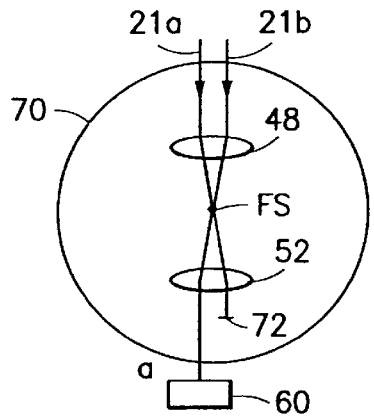
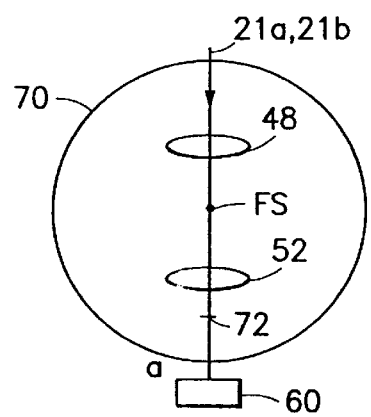
FIG. 3c  FIG. 3d
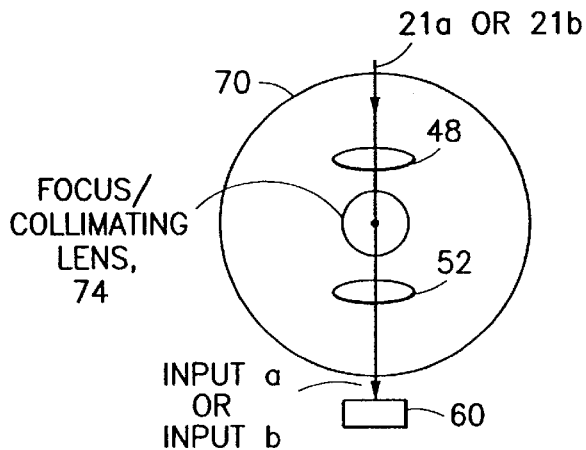
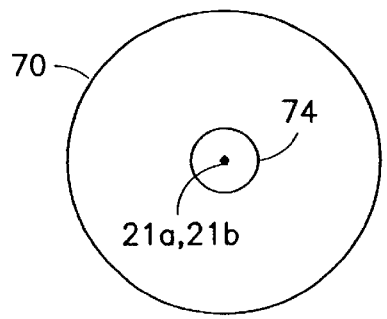
FIG. 3e  FIG. 3f

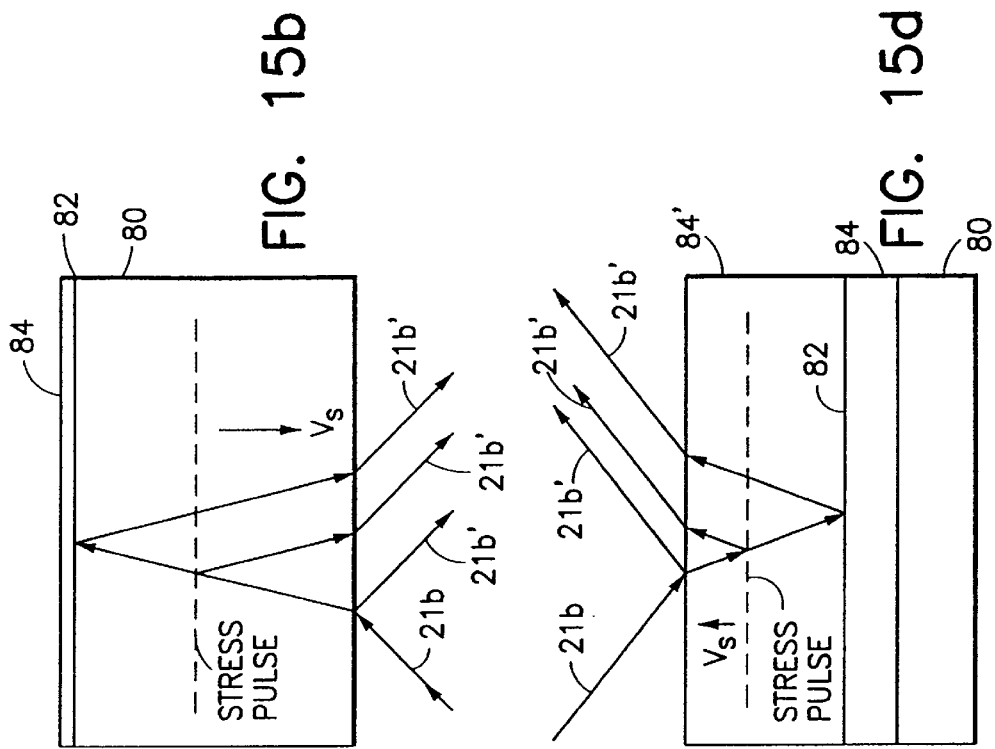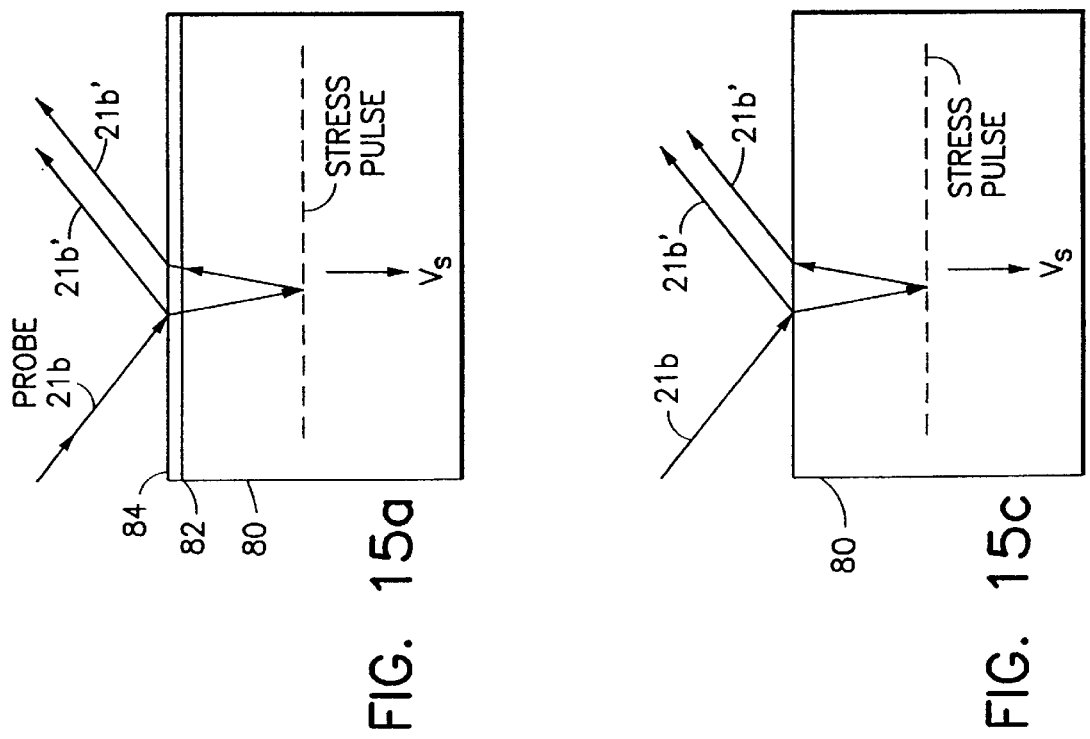

OPTICAL STRESS GENERATOR AND DETECTOR

CLAIM OF PRIORITY FROM A COPENDING PROVISIONAL PATENT APPLICATION

This is a Division of U.S. patent application Ser. No. 09/382,251, filed on Aug. 24, 1999, which is a Division of U.S. patent application Ser. No. 08/954,347, filed on Oct. 17, 1997, now U.S. Pat. No. 5,959,735, issued on Sep. 28, 1999, which is a Division of U.S. patent application Ser. No. 08/689,287, filed on Aug. 6, 1996, now U.S. Pat. No. 5,748,318, issued on May 5, 1998, which claims priority under 35 U.S.C. 119(e) from Provisional Patent Application No. 60/010,543, filed on Jan. 23, 1996, incorporated by reference herein in its entirety.

STATEMENT OF GOVERNMENT RIGHTS

This invention was made with government support under grant/contract number DEFG02-ER45267 awarded by the Department of Energy. The government has certain rights in the invention.

FIELD OF THE INVENTION

This invention relates to a system for measuring the properties of thin films, and more particularly to a system which optically induces stress pulses in a film and which optically measures the stress pulses propagating within the film.

BACKGROUND OF THE INVENTION

Presently, the nondestructive evaluation of thin films and interfaces is of interest to manufacturers of electrical, optical and mechanical devices which employ thin films. In one nondestructive technique a radio frequency pulse is applied to a piezoelectric transducer mounted on a substrate between the transducer and the film to be studied. A stress pulse propagates through the substrate toward the film. At the boundary between the substrate and the film, part of the pulse is reflected back to the transducer. The remainder enters the film and is partially reflected at the opposite side to return through the substrate to the transducer. The pulses are converted into electrical signals, amplified electronically, and displayed on an oscilloscope. The time delay between the two pulses indicates the film thickness, if the sound velocity in the film is known, or indicates the sound velocity, if the film thickness is known. Relative amplitudes of the pulses provide information on the attenuation in the film or the quality of the bond between the film and the substrate.

The minimum thickness of films which can be measured and the sensitivity to film interface conditions using conventional ultrasonics is limited by the pulse length. The duration of the stress pulse is normally at least 0.1 $\mu$sec corresponding to a spatial length of at least $3 \times 10^{-2}$ cm for an acoustic velocity of $3 \times 10^5$ cm/sec. Unless the film is thicker than the length of the acoustic pulse, the pulses returning to the transducer will overlap in time. Even if pulses as short in duration as 0.001 $\mu$sec are used, the film thickness must be at least a few microns.

Another technique, acoustic microscopy, projects sound through a rod having a spherical lens at its tip. The tip is immersed in a liquid covering the film. Sound propagates through the liquid, reflects off the surface of the sample, and returns through the rod to the transducer. The amplitude of the signal returning to the transducer is measured while the sample is moved horizontally. The amplitudes are converted to a computer-generated photograph of the sample surface. Sample features below the surface are observed by raising the sample to bring the focal point beneath the surface. The lateral and vertical resolution of the acoustic microscope are approximately equal.

Resolution is greatest for the acoustic microscope when a very short wavelength is passed through the coupling liquid. This requires a liquid with a low sound velocity, such as liquid helium. An acoustic microscope using liquid helium can resolve surface features as small as 500 Angstroms, but only when the sample is cooled to 0.1 K.

Several additional techniques, not involving generation and detection of stress pulses, are available for measuring film thickness. Ellipsometers direct elliptically polarized light at a film sample and analyze the polarization state of the reflected light to determine film thickness with an accuracy of 3–10 Angstroms. The elliptically polarized light is resolved into two components having separate polarization orientations and a relative phase shift. Changes in polarization state, beam amplitudes, and phase of the two polarization components are observed after reflection.

The ellipsometer technique employs films which are reasonably transparent. Typically, at least 10% of the polarized radiation must pass through the film. The thickness of metal sample films thus cannot exceed a few hundred Angstroms.

Another technique uses a small stylus to mechanically measure film thickness. The stylus is moved across the surface of a substrate and, upon reaching the edge of a sample film, measures the difference in height between the substrate and the film. Accuracies of 10–100 Angstroms can be obtained. This method cannot be used if the film lacks a sharp, distinct edge, or is too soft in consistency to accurately support the stylus.

Another non-destructive method, based on Rutherford Scattering, measures the energy of backscattered helium ions. The lateral resolution of this method is poor.

Yet another technique uses resistance measurements to determine film thickness. For a material of known resistivity, the film thickness is determined by measuring the electrical resistance of the film. For films less than 1000 Angstroms, however, this method is of limited accuracy because the resistivity may be non-uniformly dependent on the film thickness.

In yet another technique, the change in the direction of a reflected light beam off a surface is studied when a stress pulse arrives at the surface. In a particular application, stress pulses are generated by a piezoelectric transducer on one side of a film to be studied. A laser beam focused onto the other side detects the stress pulses after they traverse the sample. This method is useful for film thicknesses greater than 10 microns.

A film may also be examined by striking a surface of the film with an intense optical pump beam to disrupt the film's surface. Rather than observe propagation of stress pulses, however, this method observes destructive excitation of the surface. The disruption, such as thermal melting, is observed by illuminating the site of impingement of the pump beam with an optical probe beam and measuring changes in intensity of the probe beam. The probe beam's intensity is altered by such destructive, disruptive effects as boiling of the film's surface, ejection of molten material, and subsequent cooling of the surface.

See Downer, M. C.; Fork, R. L.; and Shank, C. V., "Imaging with Femtosecond Optical Pulses", Ultrafast Phenomena IV, Ed. D. H. Auston and K. B. Eisenthal (Spinger-Verlag, N.Y. 1984), pp. 106–110.

Other systems measure thickness, composition or concentration of material by measuring absorption of suitably-chosen wavelengths of radiation. This method is generally applicable only if the film is on a transparent substrate.

In a nondestructive ultrasonic technique described in U.S. Pat. No. 4,710,030 (Tauc et al.), a very high frequency sound pulse is generated and detected by means of an ultrafast laser pulse. The sound pulse is used to probe an interface. The ultrasonic frequencies used in this technique typically are less than 1 THz, and the corresponding sonic wavelengths in typical materials are greater than several hundred Angstroms. It is equivalent to refer to the high frequency ultrasonic pulses generated in this technique as coherent longitudinal acoustic phonons.

In more detail, Tauc et al. teach the use of pump and probe beams having durations of 0.01 to 100 psec. These beams may impinge at the same location on a sample's surface, or the point of impingement of the probe beam may be shifted relative to the point of impingement of the pump beam. In one embodiment the film being measured can be translated in relation to the pump and probe beams. The probe beam may be transmitted or reflected by the sample. In a method taught by Tauc et al. the pump pulse has at least one wavelength for non-destructively generating a stress pulse in the sample. The probe pulse is guided to the sample to intercept the stress pulse, and the method further detects a change in optical constants induced by the stress pulse by measuring an intensity of the probe beam after it intercepts the stress pulse.

In one embodiment a distance between a mirror and a corner cube is varied to vary the delay between the impingement of the pump beam and the probe beam on the sample. In a further embodiment an opto-acoustically inactive film is studied by using an overlying film comprised of an opto-acoustically active medium, such as arsenic telluride. In another embodiment the quality of the bonding between a film and the substrate can be determined from a measurement of the reflection coefficient of the stress pulse at the boundary, and comparing the measured value to a theoretical value.

The methods and apparatus of Tauc et al. are not limited to simple films, but can be extended to obtaining information about layer thicknesses and interfaces in superlattices, multilayer thin-film structures, and other inhomogeneous films. Tauc et al. also provide for scanning the pump and probe beams over an area of the sample, as small as 1 micron by 1 micron, and plotting the change in intensity of the reflected or transmitted probe beam.

While well-suited for use in many measurement applications, it is an object of this invention to extend and enhance the teachings of Tauc et al.

OBJECTS OF THE INVENTION

It is thus an object of this invention to provide an improved optical generator and detector of stress pulses.

It is a further object of this invention to provide an improved ultrafast optical technique for measuring stress in a thin film.

It is still another object of this invention to provide an improved ultrafast optical technique for determining the elastic modulus, sound velocity, and refractive index of a thin film.

It is a still further object of this invention to provide an improved ultrafast optical technique for characterizing an interface between two materials, such as an interface between a substrate and an overlying thin film.

It is another object of this invention to provide an ultrafast optical technique for determining a derivative of a transient response of a sample to a pump pulse, and for correlating the derivative with a characteristic of interest, such as the static stress within the sample.

It is another object of this invention to provide an ultrafast optical technique for varying a temperature of the sample and, while varying the temperature, for determining a derivative of the acoustic velocity within the sample and for subsequently correlating the derivative of the acoustic velocity with the static stress within the sample.

It is another object of this invention to provide an ultrafast optical technique for determining an electrical resistivity of a sample.

It is a further object of this invention to provide simulation methods for modelling a time-evolved effect of a stress pulse generated within a sample of interest, and to then employ the model to characterize the sample.

It is a further object of this invention to provide an ultrafast optical technique for measuring a characteristic of interest in a patterned, periodic, multilayered structure.

It is one still further object of this invention to provide an ultrafast optical system and technique wherein optical fibers are used to advantage for directing and/or focussing at least one of an incident pump beam, and incident probe beam, or a reflected or transmitted probe beam.

It is another object of this invention to provide a non-destructive system and method for simultaneously measuring at least two transient responses of a structure to a pump pulse, the measured transient responses comprising at least two of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \delta$ of the probe pulse.

It is one further object of this invention to provide a non-destructive system and method for determining a characteristic of a sample that includes an automatic control over the focussing of pump and probe beams at the sample so as to provide a reproducible intensity variation of the beams during each measurement.

SUMMARY OF THE INVENTION

The foregoing and other problems are overcome and the objects of the invention are realized by methods and apparatus in accordance with embodiments of this invention.

This invention relates to a system for the characterization of thin films and interfaces between thin films through measurements of their mechanical, optical, and thermal properties. In the system of this invention incident light is absorbed in a thin film or in a structure made up of several thin films, and the change in optical transmission or reflection is measured and analyzed. The change in reflection or transmission is used to give information about the ultrasonic waves that are produced in the structure. The information that is obtained from the use of the measurement methods and apparatus of this invention can include: (a) a determination of the thickness of thin films with a speed and accuracy that is improved compared to earlier methods; (b) a determination of the thermal, elastic, electrical, and optical properties of thin films; (c) a determination of the stress in thin films; and (d) a characterization of the properties of interfaces, including the presence of roughness and defects.

The invention features a radiation source for providing a pump beam and a detection system for non-destructively measuring the properties of one or more interfaces within a sample. The radiation source provides the pump beam so as to have short duration radiation pulses having an intensity and at least one wavelength selected to non-destructively induce a propagating stress wave in the sample, a radiation source for providing a probe beam, a mechanism for directing the pump beam to the sample to generate the stress wave within the sample, and a mechanism for guiding the probe beam to a location at the sample to intercept the stress wave. A suitable optical detector is provided that is responsive to a reflected or transmitted portion of the probe beam for detecting a change in the optical constants of the material induced by the stress wave.

In one embodiment, the optical detector measures the intensity of the reflected or transmitted probe beam. The pump and probe beam may be derived from the same source that generates a plurality of short duration pulses, and the system further includes a beam splitter for directing a first portion of the source beam to form the pump beam, having the plurality of pulses, and directing a second portion to form the probe beam, also having the plurality of pulses. The source beam has a single direction of polarization and the system further includes means for rotating the polarization of the probe beam and a device, disposed between a sample and the optical detector, for transmitting only radiation having the rotated direction of polarization. The system may further include a temperature detector and a chopper for modulating the pump beam at a predetermined frequency. The system can further include a mechanism for establishing a predetermined time delay between the impingement of a pulse of the pump beam and a pulse of the probe beam upon the sample. The system can further include circuitry for averaging the output of the optical detector for a plurality of pulse detections while the delay between impingements remains set at the predetermined time delay. The delay setting mechanism may sequentially change the predetermined time delay and the circuitry for averaging may successively average the output of the optical detector during each successive predetermined time delay setting.

By example, the pump beam may receive 1% to 99% of the source beam, and the source beam may have an average power of 10 $\mu$W to 10 kW. The source beam may include wavelengths from 100 Angstroms to 100 microns, and the radiation pulses of the source beam may have a duration of 0.01 psec to 100 psec.

The sample may include a substrate and at least one thin film to be examined disposed on the substrate such that interfaces exist where the films meet, and/or where the film and the substrate meet. For a sample with an optically opaque substrate, at the pump wavelength, the pump and probe beams may both impinge from the film side, or the pump may impinge from the film side and the probe may impinge from the substrate side. For a sample with a transparent substrate, both beams may impinge from the film side, or from the substrate side, or from opposite sides of the sample. The optical and thermal properties are such that the pump pulse changes the temperature within at least one film with respect to the substrate. The temperature within one or more of the thin films disposed on the substrate may be uniform, and may be equal in several films. The films may have thicknesses ranging from 1 Å to 100 microns. At least one film in the sample and/or the substrate has the property that when a stress wave is present it causes a change in the intensity, optical phase, polarization state, position, or direction of the probe beam at the detector. The probe beam source may provide a continuous radiation beam, and the pump beam source may provide at least one discrete pump pulse having a duration of 0.01 to 100 psec and an average power of 10 $\mu$W to 1 kW. Alternatively the probe beam source may provide probe beam pulses having a duration of 0.01 to 100 psec, the pump beam and probe beam may impinge at the same location on the sample, and the mechanisms for directing and guiding may include a common lens system for focusing the pump beam and the probe beam onto the sample. The position of impingement of the probe beam may be shifted spatially relative to that of the pump beam, and the probe beam may be transmitted or reflected by the sample.

One or more fiber optic elements may be incorporated within the system. Such fibers may used to guide one or more beams within the system for reducing the size of the system, and/or to achieve a desired optical effect such as focussing of one or more beams onto the surface of the sample. To achieve focussing, the fiber may be tapered, or may incorporate a small lens at its output. A similar focussing fiber can be used to gather reflected probe light and direct it to an optical detector. A fiber may also be used to modify the beam profile, or as a spatial filter to effect a constant beam profile under widely varying input beam conditions.

This invention advantageously provides a non-destructive system and method for measuring at least one transient response of a structure to a pump pulse of optical radiation, the measured transient response or responses including at least one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \delta$ of the probe pulse, each of which may be considered as a change in a characteristic of a reflected or transmitted portion of the probe pulse. The measured transient response or responses are then associated with at least one characteristic of interest of the structure.

In a presently preferred embodiment the system provides for automatically focusing the pump and probe pulses to achieve predetermined focusing conditions, and the application of at least one calibration factor to the at least one transient response. This embodiment is especially useful when employed with time-evolved simulations and models of a structure of interest, which is a further aspect of this invention.

BRIEF DESCRIPTION OF THE DRAWINGS

The above set forth and other features of the invention are made more apparent in the ensuing Detailed Description of the Invention when read in conjunction with the attached Drawings, wherein:

FIGS. 3a–3f each depict an embodiment of a pump beam/probe beam delivery technique to a surface of a sample;

FIG. 4b is block diagram that illustrates an embodiment of electro-optical components responsive to the delay between the pump and probe pulses, as shown in FIG. 4a;

FIGS. 15a–15d each illustrate an optically-induced stress wave, having a velocity $v_s$, that propagates in a material, and the reflection of a portion of the probe beam from the stress wave;

DETAILED DESCRIPTION OF THE INVENTION

The disclosure of the above-referenced U.S. Pat. No. 4,710,030 (Tauc et al.) is incorporated by reference herein in its entirety.

The teaching of this invention is embodied by an optical generator and detector of a stress wave within a sample. In this system a first non-destructive pulsed beam of electromagnetic radiation is directed upon a sample containing at least one film and possibly also an interface between similar or dissimilar materials. The first pulsed beam of electromagnetic radiation, referred to herein as a pump beam 21a, produces a propagating stress wave within the sample. A second non-destructive pulsed beam of electromagnetic radiation, referred to herein as a probe beam 21b, is directed upon the sample such that at least one of the polarization, optical phase, position, direction and intensity of a reflected portion of the probe beam 21b' or a transmitted portion of the probe beam 21b" is affected by a change in the optical constants of the materials comprising the sample, or by a change in the thickness of one or more layers or sublayers within a thin film sample due to a propagating stress wave. Physical and chemical properties of the materials, and possibly also of the interface, are measured by observing the changes in the reflected or transmitted probe beam intensity, direction, or state of polarization as revealed by the time dependence of the changes in beam intensity, direction or state of polarization. The very short time scale is particularly important for achieving a high sensitivity to interfacial and other properties, and for measuring the properties of films having thicknesses less than several microns.

Figure 10:
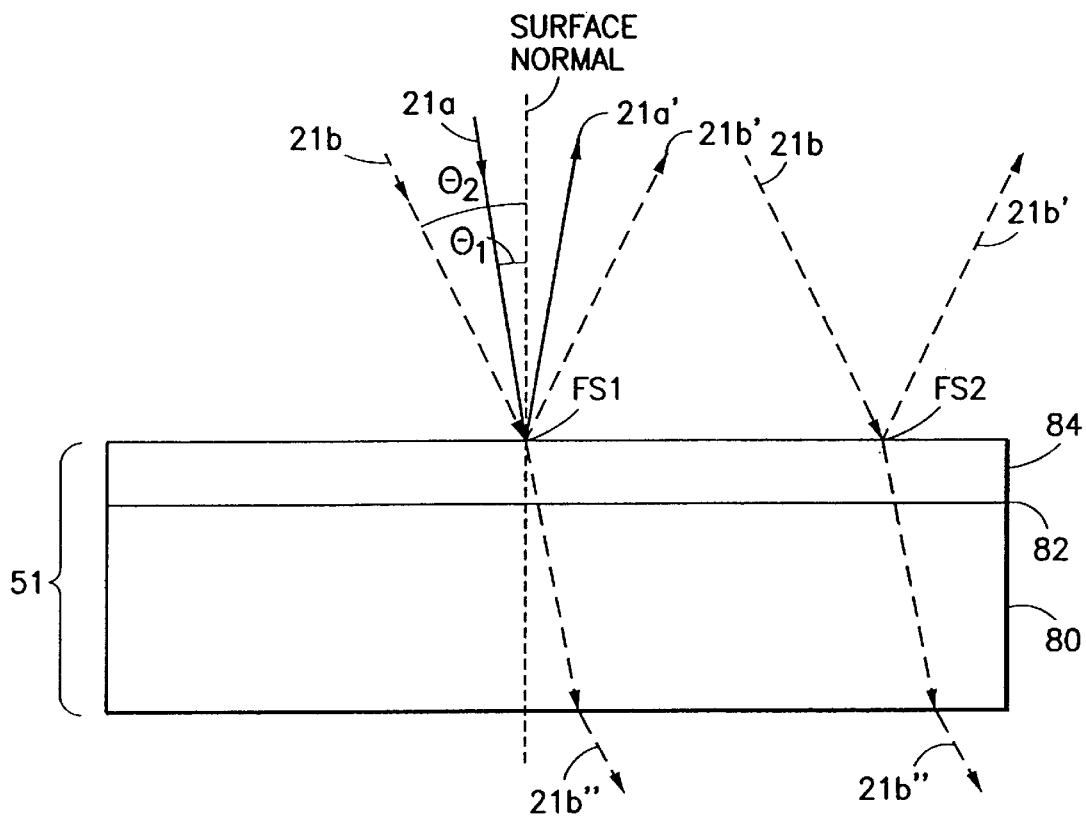
FIG. 10 is a cross-sectional, enlarged view of the sample having the substrate, thin film layer, and the interface between the substrate and the thin film layer, and that further illustrates the impingement of the probe beam within a focussed spot (FS1) of the pump beam, and the impingement of the probe beam at a second FS (FS2) that is displaced from FS1.
Figure 11:
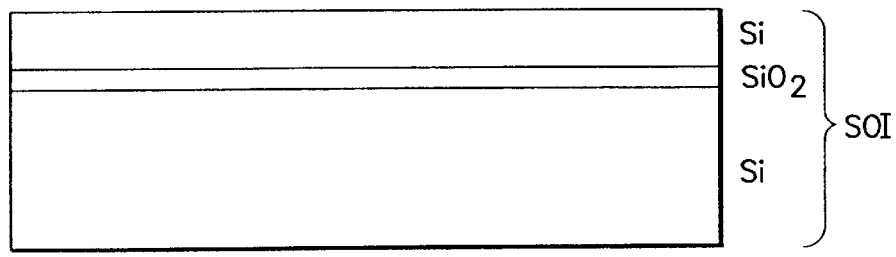
FIG. 11 is an enlarged, cross-sectional view of a silicon-on-insulator (SOI) sample that is amenable to characterization in accordance with this invention.

By way of introduction, the arrangement of the pump and probe beam according to this invention is illustrated in FIG. 10. A test sample 51 is shown comprised of a film 84 disposed on substrate 80. An interface 82 is formed between the film 84 and the substrate 80. By example, the substrate 80 may be comprised of a semiconductor such as silicon and may form a portion of a semiconductor wafer, and the film 84 may be an overlying layer of oxide, polymer, metal, or another semiconductor. In another exemplary embodiment the sample may be a SOI wafer comprised of a silicon substrate, a thin layer of silicon oxide, and an overlying (typically thin) layer of silicon, as is shown in FIG. 11. To test the sample 51 the pump beam 21a is directed onto a position on the film 84 (referred to as a focal spot FS1) to generate a stress wave in the sample due to the absorption of energy in the film 84 or substrate 80. The pump beam 21a is incident on the sample 51 at an angle $\theta_1$ offset from normal. The unabsorbed portion of the pump beam is reflected as the reflected pump beam 21a'. The probe beam 21b may be directed to the same spot (FS1) on the sample at an angle $\theta_2$ to intercept the stress pulse generated by the pump beam 21a. In other embodiments of the invention the probe beam 21b can be directed to another location (FS2). A portion of the probe beam 21b reflects from the film 84 as the reflected probe beam 21b'. Any portion of the probe beam 21b that is transmitted through the sample is referred to as the transmitted probe beam 21b". The actual values of angles $\theta_1$ and $\theta_2$ can be selected from a wide range of angles. The intensities of the reflected and transmitted pump and probe beams depend on the optical constants of the film 84 and substrate 80 and on the thicknesses of the films.

FIG. 10 also illustrates probing at points (FS2) at a distance from the pump beam FS1, which applies to the ultrasonic and all other applications disclosed herein.

For a sufficiently thick opaque film disposed on a substrate the pump light will be absorbed in a surface layer of thickness small compared to the film thickness. The absorption in the surface layer generates a stress pulse which propagates back and forth in the film, giving rise to a series of equally-separated features ("echoes") in the responses measured by the probe beam. The thickness of a simple film that is thick enough to have distinct echoes can be determined from the echo time, as described by Tauc et al. For a thinner film, the echoes become so closely spaced that they degenerate into vibrational thickness modes of the film, appearing as damped oscillations in the data, and the thickness can be deduced from the vibration period. For intermediate thickness films, or for films composed of multiple layers, the data may be too complicated to analyze so simply. In such cases it is preferred to construct a theoretical model for the vibrating structure in which there may be one or more adjustable unknowns (e.g. film thicknesses, densities, sound velocities). The theoretical model is used to simulate the vibrations of the structure over a suitable time interval (in discrete time steps), and to calculate the corresponding change in the optical reflectivity of the sample (or transmission, or polarization state, or optical phase of the transmitted or reflected beams caused by the stress induced change in the optical constants of the sample, or by stress induced displacements of the surface or of interfaces within the structure). The duration of the time steps are preferably selected to be small compared to a time required for an acoustic wave to propagate through a thinnest layer of the structure (e.g., 0.1 psec to 200 psec). By example, the duration of each time step can be established at less than one half (e.g., one tenth) of the propagation time through the thinnest layer. Also by example, the duration of each time step can be selected to be small compared to a shortest absorption length (penetration depth) for the pump or probe light in the structure.

Figure 21:
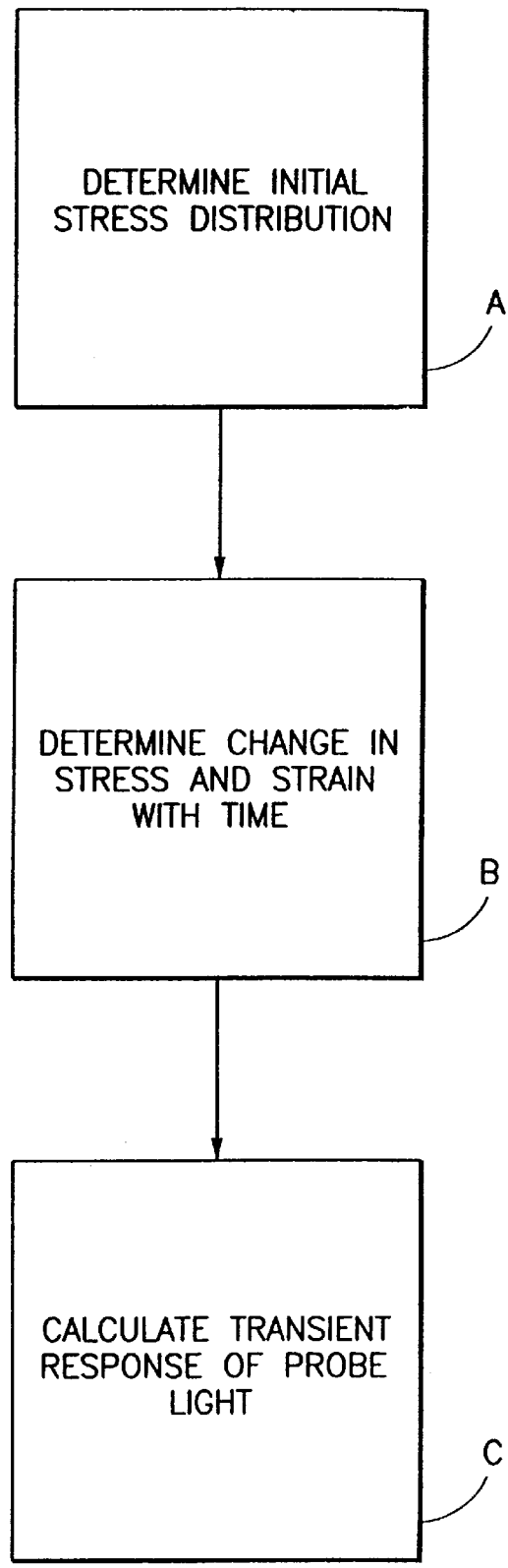
FIG. 21 is a logic flow diagram that illustrates a simulation method in accordance with an aspect of this invention.

A method for finding any number of unknowns is to compute a simulated optical response for a particular set of parameters, and then to adjust the values of the parameters as needed to achieve a best-fit to the measured result. Presently preferred methods for carrying out this modelling and simulation are described in detail below with reference to FIG. 21.

The basic equations for the vibrational part of the simulations are taken from well-known continuum elasticity theory. The basic equations for the optical part of the simulation are the Fresnel equations. As an illustration in one dimension (i.e. for a sample 51 with a stress wave propagating with velocity $v_s$ along a direction z normal to the surface), the quantity to be computed in the simulation can be written as follows:

$$\Delta R(t) = \int_0^\infty f(z) \eta_{33}(z, t) dz \quad (1)$$

In this equation f(z) is the change in the reflectivity with strain associated with stress $\eta_{33}(z,t)$ at depth z. $\Delta R(t)$ is the strain induced change in the optical reflectivity of the sample at a time t. Similar equations can be written for changes in the transmission or in the polarization state of the probe beam 21b. The function f(z) includes the effect of strain on the optical constants within the sample 51, as well as the effect of displacement of the surface or internal interfaces (i.e. a time-dependent change in the thickness of one or more layers) due to the presence of a stress wave.

In accordance with an aspect of this invention, the physical properties of the sample 51 which may be determined in this way include properties which may affect the time dependence of ultrasonic signals, and/or their amplitudes. These are (among others) layer thicknesses, sound velocities, interfacial roughness, interfacial adhesion strength, thermal diffusivities, stress, strain, optical constants, surface roughness, and interfacial contaminants.

Figure 1A:
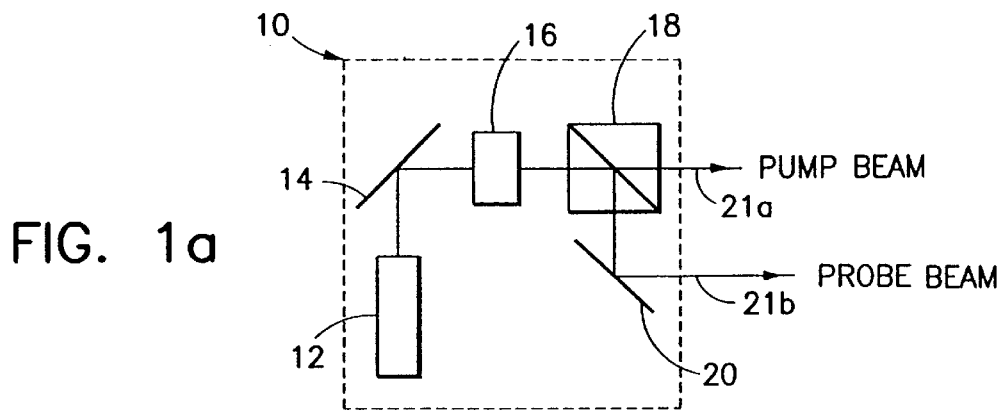
FIGS. 1a–1c depict embodiments of optical sources for use with the system of this invention.
Figure 1B:
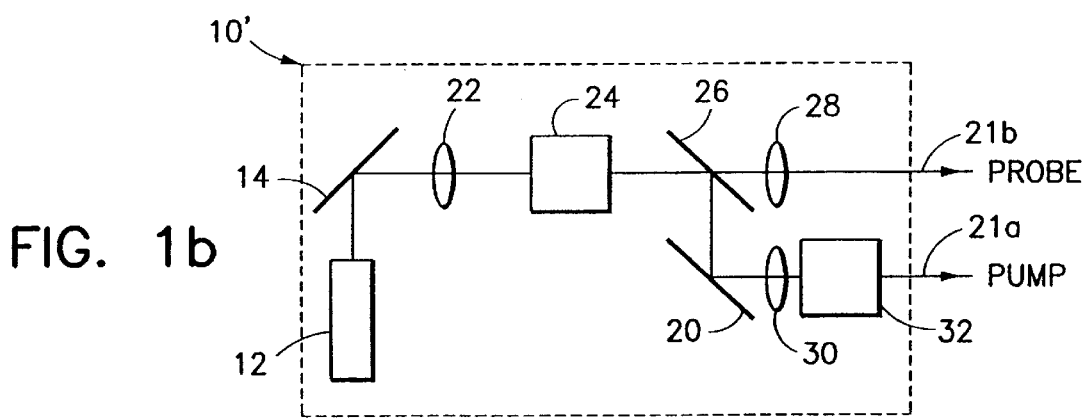
Figure 1C:
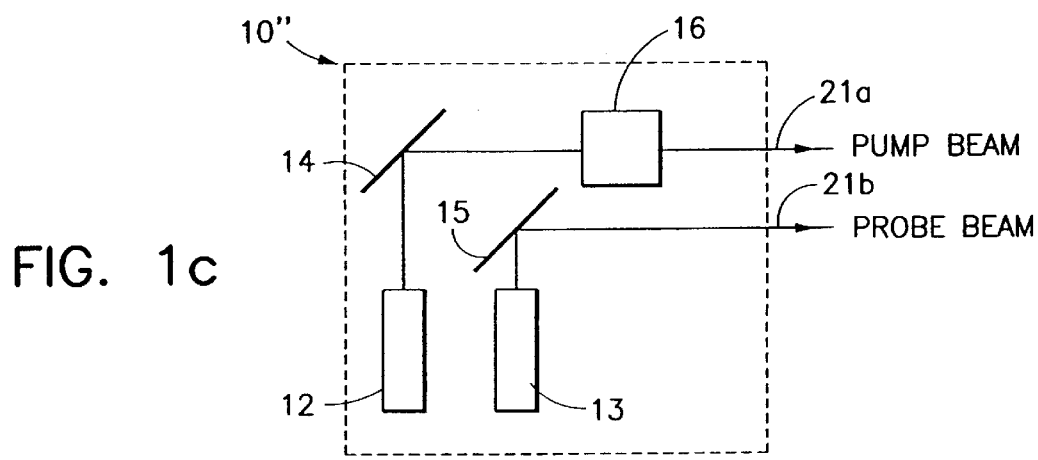
Figure 2:
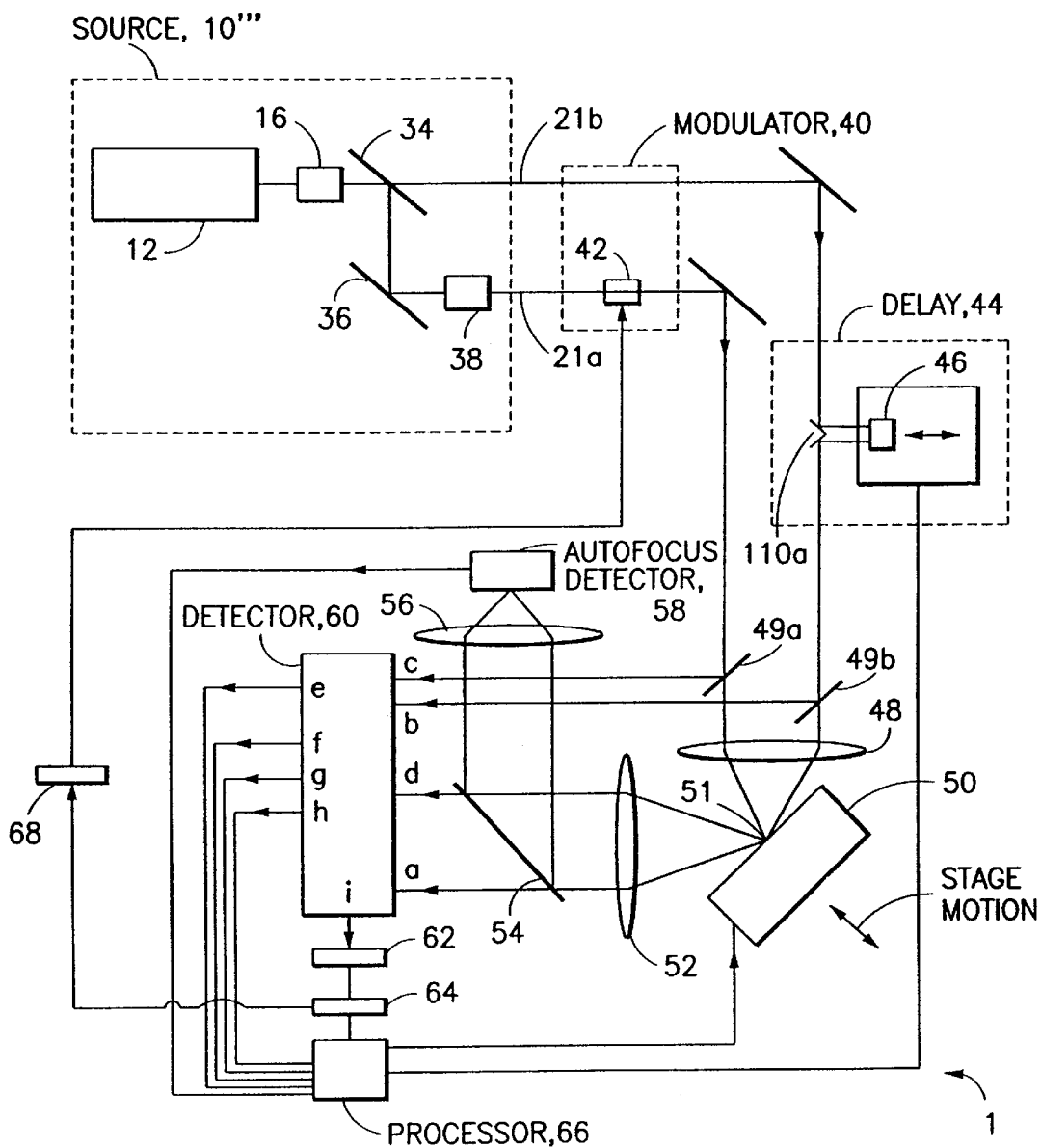
FIG. 2 is a block diagram of an embodiment of a sample characterization system in accordance with this invention.

FIGS. 1a–1c illustrate various embodiments of optical sources that are suitable for practicing this invention, while FIG. 2 is a block diagram of an optical generation and detection system for performing non-destructive picosecond time-scale thin film and interface characterizations, referred to hereinafter as system 1.

A first embodiment of an optical source 10 is shown in FIG. 1a, in which the beam from a laser 12 is reflected from a mirror 14 and passes through a polarization rotating device, such as a half-wave plate 16, to a polarizing beam splitter 18. The beams emerging from the polarizing beam splitter 18 are orthogonally polarized, and the ratio of their intensities may be varied through a wide range by adjusting the orientation of the half-wave plate 16. One beam forms the pump beam 21a, while the probe beam 21b reflects from a mirror 20.

An alternative embodiment of an optical source 10' shown in FIG. 1b includes a frequency doubling crystal 24, such as BBO or LBO, onto which the laser light is focused by a lens 22 positioned between it and the laser 12. The coaxial beams of light emerging from the frequency doubling crystal 24 are separated by means of a dichroic mirror 26 into the pump and probe beams, each of which is then collimated by lenses 28 and 30. The polarization of the pump beam 21a is rotated to be perpendicular to that of the probe beam 21b by means of a half-wave plate 32. The dichroic mirror 26 may be chosen to pass the fundamental frequency of the laser 12 and reflect the second harmonic, giving a probe beam at the fundamental and a pump beam at the second harmonic. Alternatively, the dichroic mirror 26 may be chosen to pass the second harmonic and reflect the fundamental, giving the probe beam 21b at the second harmonic and the pump beam 21a at the fundamental, as shown in FIG. 1b.

Figure 4A:
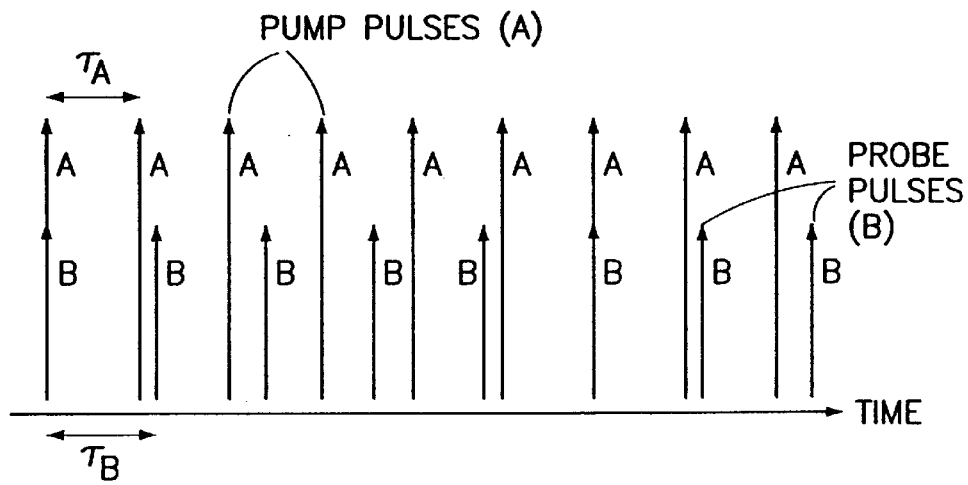
FIG. 4a is a diagram that illustrates a variability in a temporal offset between pump and probe beam pulses.

Another embodiment of an optical source 10" shown in FIG. 1c, in which the pump and probe beams are produced by two different lasers 12 and 13. In one embodiment, these may be identical pulsed lasers, in which case the upper beam is passed through the half-wave plate 16 to rotate its polarization relative to that of the lower beam by 90 degrees. Alternatively, the lasers 12 and 13 may emit dissimilar wavelengths (two "colors"). Alternatively, the probe laser 13 may emit a continuous (i.e. non-pulsed) beam. Alternatively, the pump laser 12 may emit pulses with a repetition period of $\tau_A$ and the probe laser 13 may emit pulses with a repetition period $\tau_B$, as shown in FIG. 4a. Such a scheme may be used to effect a continuously variable delay between the pump and probe pulses without the use of a mechanical delay stage 44 of a type depicted in FIG. 2.

Figure 4B:
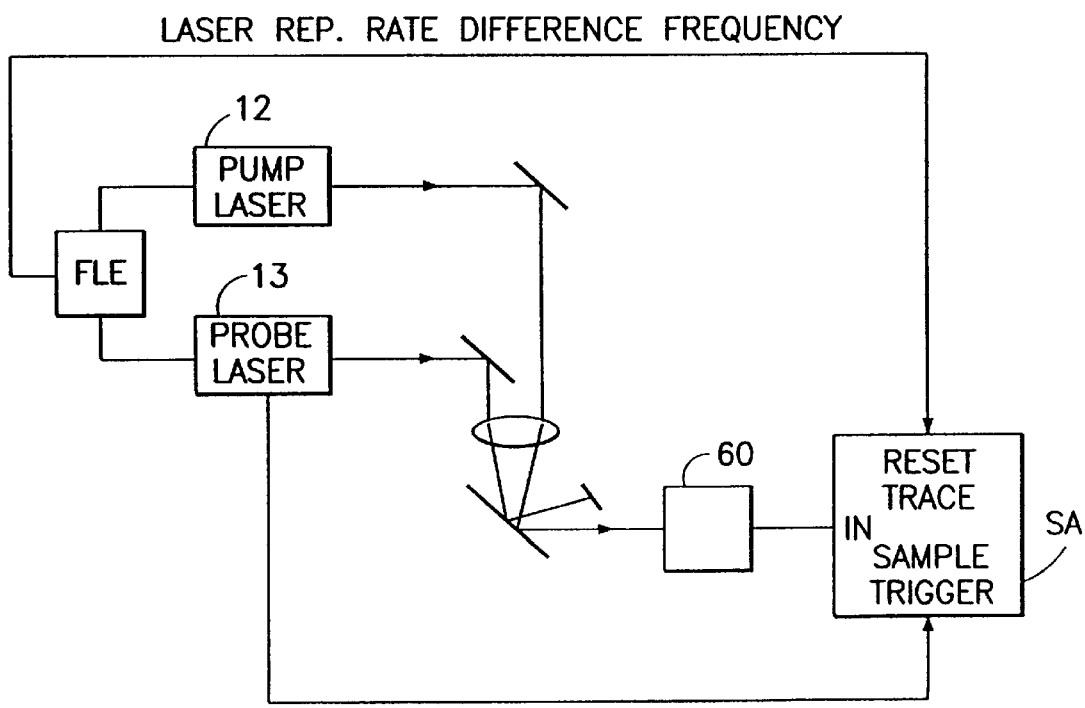

Referring now to FIG. 4b, in this alternative technique the delay between pairs of A and B pulses increases by a time $\tau_B-\tau_A$ from one repetition to the next. By example, $\tau_B-\tau_A$ may be 0.1 psec on average, and the repetition rate of the pump laser 12 may be 100 MHz. This gives a time between simultaneous arrivals of the pump and probe pulses of one millisecond (i.e., the scan time). This embodiment further includes suitable frequency locking electronics (FLE), mirrors, a lens, a suitable detector 60, and a fast signal averager (SA). A measurement of, by example, $\Delta R(t)$ may be performed by applying a signal corresponding to the reflected probe intensity from the output of the detector 60 to the input of the fast signal averager (SA), and by triggering sample acquisitions at times corresponding to the pulsing of the probe laser 13. A large number (e.g., thousands) of measurements may be averaged in order to effect a desired signal to noise ratio. It should be noted in regard to this invention that the delay stage and modulator described previously in regard to FIG. 2 may be omitted. It should also be appreciated that any "jitter" in the pulsing of the two lasers may have the effect of averaging the signals corresponding to closely spaced delay times, and that this effect may somewhat attenuate the high frequency components of the measurement.

Although the pump and probe lasers are depicted in FIG. 1c separately, they may have one or more optical elements in common, including the gain medium. Other permutations of pump and probe color, polarization and pulse rate suggested by the above description may be used to achieve an improvement in signal quality, depending on the properties of the materials to be investigated.

Examples of the pulsed lasers suitable for use in the system 1 include an Argon ion pumped solid state modelocked laser, such as Coherent Inc. Inova (Argon) and Mira (Ti:sapphire); a diode laser pumped solid state mode locked laser, such as a continuous wave diode pumped frequency doubled YAG and modelocked Ti:sapphire laser; and a direct diode pumped mode-locked solid state laser.

Referring to the embodiment of FIG. 2, a further embodiment of an optical source 10''' provides both the pump and probe beams 21a and 21b, respectively, in a manner similar to the embodiment of FIG. 1a. In the FIG. 2 arrangement the linearly polarized beam from laser 12 passes through the half-wave plate 16, which is used to rotate its polarization. The polarized beam is then split into pump and probe beams by a dielectric beam splitter 34. The ratio of pump to probe may be varied by rotating the incoming polarization. The lower beam is the pump beam 21a, and the upper beam is the probe beam 21b. The pump beam 21a passes through a half-wave plate/polarizer combination 38 which rotates its polarization to be orthogonal to that of the probe beam 21b, and which also suppresses any light not polarized along this orthogonal axis.

The pump and probe beams 21a and 21b are emitted by the source, and the intensity of the pump beam is modulated at a rate of about 1 MHz by an acousto-optic modulator (AOM) 40, or by a photoelastic modulator followed by a polarizer, or by other intensity modulation means. The probe beam path length is varied by translating a retroreflector 46 mounted on a computer-controlled delay stage 44, via a steering mirror combination 110a. Both beams are then focused by lens 48 onto the sample 51 mounted on a translatable sample stage 50, and are detected by a photodetector 60. In this embodiment the inputs to the detector 60 include portions of the input pump and probe beams (inputs c and b, respectively, via beam splitters 49a and 49b, respectively); and also include portions of the reflected pump beam 21a' and reflected probe beam 21b' (inputs d and a, respectively). Outputs from the detector 60 include signals proportional to the incident pump beam intensity (e); incident probe beam intensity (f) reflected pump beam intensity (g); reflected probe beam intensity (h); and probe modulation intensity (i), i.e. only the modulated part of the reflected probe intensity. These detector outputs are fed into a processor 66. The processor 66 calculates from the inputs the fractional change in the sample's reflectivity R (i.e. $\Delta R/R$), and normalizes this change by the intensity of the incident pump beam.

In the apparatus of this invention the detector input designated as (a) contains a modulated component which carries the stress information in addition to a large unmodulated reflected probe component 21b'. Input (b) is proportional to the unmodulated portion of the probe signal 21b. The output (i) is a voltage proportional to only the modulated part of the probe signal, which is determined by electronically removing the unmodulated component from the input (a). This output goes to a bandpass filter and preamplifier 62, then to a synchronous demodulator 64 (e.g. a lockin amplifier), and finally to the processor 66 where it is digitized and stored. The inputs (a) and (b) are also used to determine the reflectivity of the sample corresponding to the probe beam 21b, and similarly inputs (d) and (c) are used to determine the reflectivity of the sample corresponding to the pump beam 21a. These quantities may be used to validate the optical simulation of the structure, or in some cases to deduce layer properties such as thickness in accordance with known optical reflectometry principles. In addition, inputs (a) and (d) are used by the processor 66 to normalize the reflectivity change output (i). The energy deposited in the sample 51 by the pump beam 21a may be determined by comparing the incident and reflected pump and probe beam intensities (21a', 21b').

Portions of the pump and probe beams may also be directed via beam splitter 54 onto one or more position sensitive detectors (autofocus detector 58) whose output may be used by the processor 66, in conjunction with the sample translation stage 50, to effect an optimum focus of the pump and probe beams on the sample 51. The signal to noise ratio may be improved by placing color filters and/or polarizers between the sample 51 and detector 60 to prevent light scattered from other parts of the system from impinging one or more detectors (as an example, to prevent pump light scattered from the sample 51 from impinging on reflected probe intensity detector (a)). The signal quality may be further improved by passing the modulated probe intensity output (i) from the detector 60 through the synchronous demodulator 64 (such as a lockin amplifier, or signal averager) located before the processor 66. The signal quality may be further improved for samples 51 tending to scatter the pump beam 21a into the probe detector by introducing a second intensity modulator into the probe beam path between the source 10 and the sample 51. The second intensity modulator has a modulation frequency differing from the pump beam modulation frequency by an amount such that the difference frequency is greater than the input bandwidth of the synchronous demodulator 62. The detector output (i) corresponding to the reflected probe intensity may then be synchronously demodulated at the difference frequency, while the components of. (i) at the modulation frequencies are rejected.

The pump and probe beams may be focused, as in FIG. 2, onto the sample through the common lens 48. This arrangement is simple to practice but is not optimal for all cases, since the pump beam 21a need be scattered through only a small angle by a non-ideal sample to impinge on the reflected probe detector (a), thereby introducing noise to the measurement of the modulated probe intensity. The common lens approach also has the weakness of achieving non-optimal spot overlap, which may be improved by using separate lenses, or coaxial beams. The common lens approach is represented in FIG. 3d in plan view from a location along a normal to the sample, here a semiconductor wafer 70. Other focusing geometries may give improved signal quality, depending on the properties of the sample (e.g. the amount of surface roughness), and the source (e.g.

pump and probe beams having different colors, versus pump and probe beams having the same color).

Figure 6:
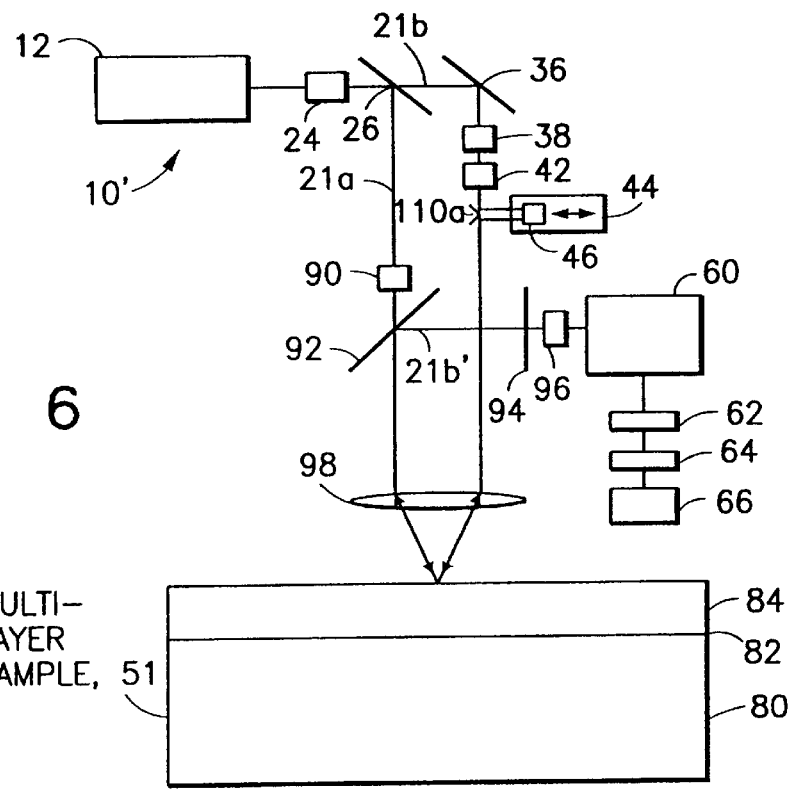
FIG. 6 illustrates a second embodiment of the interface characterization system in accordance with this invention.

Alternative focusing geometries are also illustrated in FIG. 3, and include:

(FIG. 3a) pump and probe beams oblique to the sample plane (i.e., the surface of wafer 70) and not parallel or coaxial to each other;

(FIG. 3b) pump and probe beams substantially normal to the sample plane and parallel, focused through a common lens 98 (as in FIG. 6);

(FIG. 3c) pump and probe beams parallel and lying in a plane orthogonal to the plane of incidence, focused through common lenses 48 and 52;

(FIG. 3e) (i) pump beam normal and probe beam oblique, focused independently; or (ii) probe normal and pump oblique; and (FIG. 3f) pump beam and probe beam both normal to the sample plane and coaxial, focused through a common lens 74.

Figure 9:
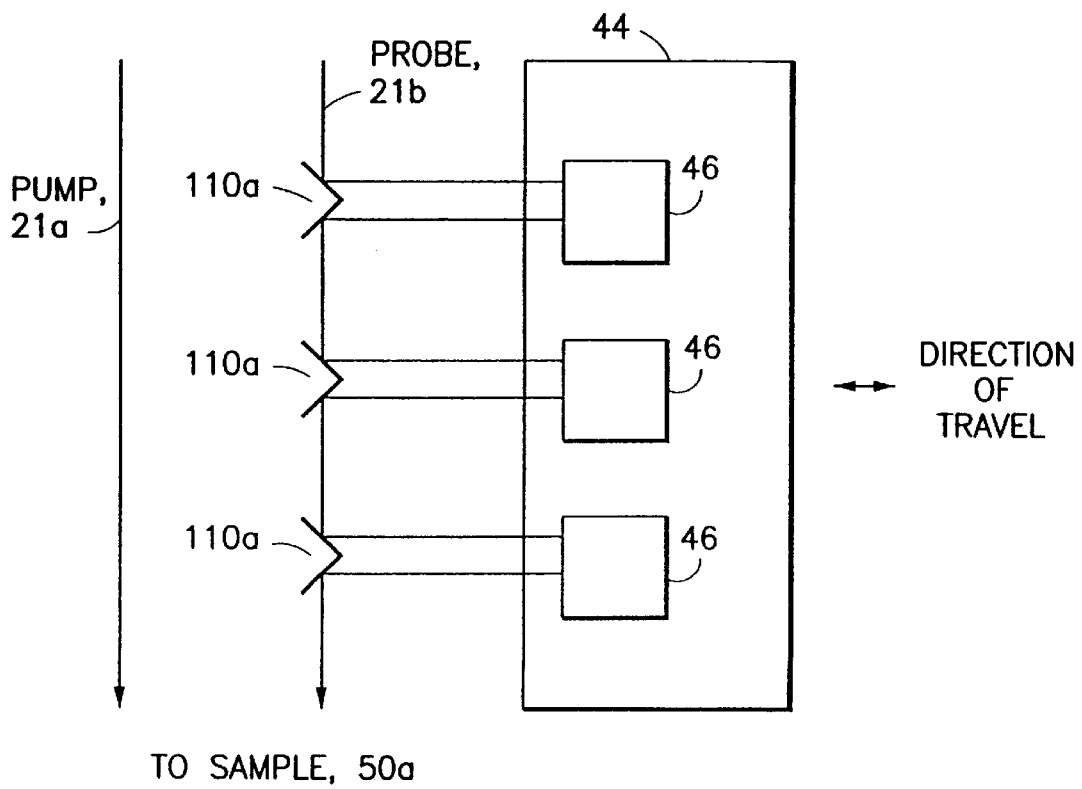
FIG. 9 illustrates an embodiment of a delay stage used for setting a delay between the pump and probe beam pulses.

The variable delay between the pump and probe beams may be implemented as shown in FIG. 2 by means of the computer controlled delay stage 44 in the probe beam path. Alternatively, a similar delay stage may be inserted within the pump beam path to "advance" the pump beam pulses in time relative to the probe pulses. An extremely long delay may be implemented as shown in FIG. 9 by placing more than one retroreflector 46 on the single translation stage 44. In this embodiment a plurality of the beam steering mirrors 110a are employed to direct the probe beam 21b to individual ones of the retroreflectors 46, thereby significantly increasing the probe beam path length relative to the pump beam path length. It is possible to implement a delay which is longer than the time between successive pulses such that the effects of a pump pulse arriving at the sample more than one pulse interval before the probe may be detected.

The shape and position of the focused probe spot FS on the surface of the sample 51 may vary systematically, depending on the position of the delay stage 44 (i.e. the time delay). For example, the system 1 may exhibit a lack of parallelism between the probe path in FIG. 2 and the delay stage axis due to misalignment, or as a result of a flaw in the stage mechanism. This causes a translation of the probe beam across the focusing lens, and for a lens exhibiting typical aberrations, can introduce a corresponding lateral translation of the probe beam 21b relative to the pump beam 21a on the surface of the sample 51, as a function of delay.

Figure 8:
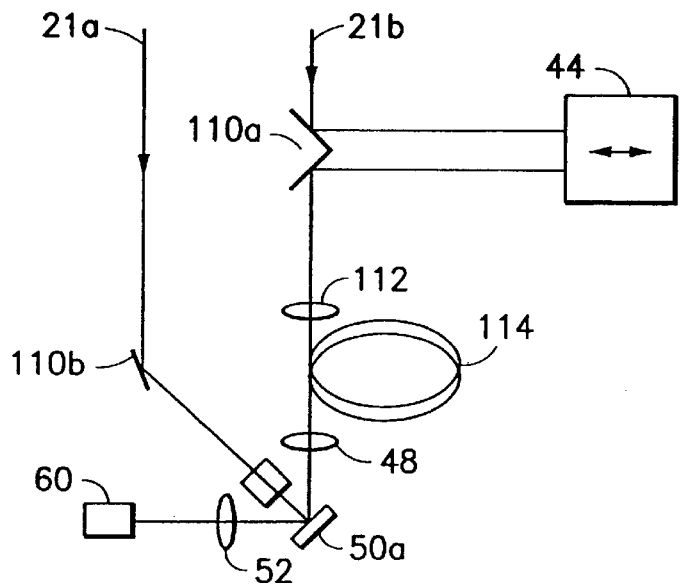
FIG. 8 illustrates a further embodiment of this invention wherein a length of fiber optic is employed to compensate for a change in probe beam profile as a function of delay between the pump and probe beam pulses.

In addition, since all laser beams exhibit some degree of divergence, varying the path length of one of the beams changes its diameter at the focusing lens, and this causes a corresponding change in the diameter of the focused spot (FS) on the sample 51. The result of all such effects may be to introduce a spurious dependence of the signal upon delay time. One method to eliminate such dependencies is shown in FIG. 8, in which a length of optical fiber 114 is introduced to the path of the delayed probe beam (or advanced pump beam). The fiber 114 serves as a spatial filter, preserving a constant spot position, size and profile throughout a range of input beam conditions. By incorporating such a device into the probe beam path it is possible to preserve a very stable overlap of the pump and probe beams on the focus spot FS over a wide range of delay stage positions. Other types of spatial filters may also be used to achieve the same effect; for example, any small aperture (typically smaller than the beam size) such as a pinhole or narrow slit, followed by a second aperture so chosen as to block high spatial Fourier components of the beam may be used. A lens may be used to focus the beam onto the first aperture, and a second lens may be used to collimate the beam emerging from the second aperture. In a system employing any of the above techniques it is preferred to monitor the intensity of the delayed (or advanced) beam either before or after it impinges on the sample, to properly normalize the final signal.

Figure 5:
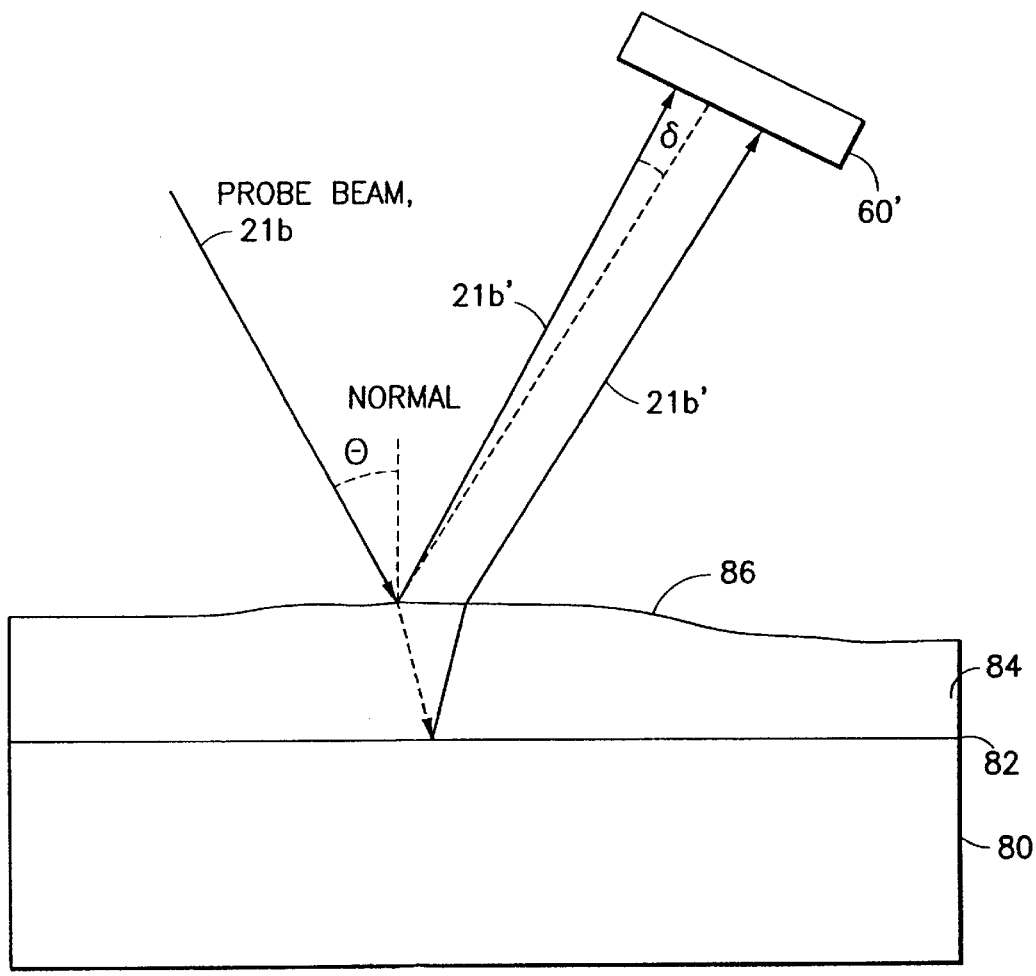
FIG. 5 is a cross-sectional, enlarged view of a sample having a substrate, a thin film layer, and an interface between the substrate and the thin film layer, and that further illustrates a stress-induced deformation in the thin film wherein constructive and destructive probe beam interference occurs.

Referring now to FIG. 5, there is illustrated a deflection through an angle θ of the probe beam 21b by a non-uniform expansion of a region wherein a propagating stress wave exists (i.e. a bulge 86 in the film 84). The bulge 86 is caused at least in part by a stress wave which may also have a non-uniform profile across the spot. The deflection can be detected by a position sensitive detector such as a split cell 60'. Movement of the reflected probe beam 21b' can also come about in the absence of the bulge 86 in transparent and semi-transparent samples due to a stress induced change in the refractive index. In this case the beam is displaced by a small amount parallel to the direction along which it would normally deflect. This displacement can also be detected by a position sensitive detector. FIG. 5 also illustrates the lengthening of the path through the sample as a result of the surface displacement (uniform or non-uniform).

FIG. 6 illustrates a configuration which is based on FIGS. 1, 2 and 3, and is a preferred implementation of a "normal incidence, dual wavelength" system. The source 10' (FIG. 1b) is frequency doubled using the nonlinear crystal 24, such as BBO, KTP or LBO. The pump and probe beams are separated by the dichroic mirror 26 such that the doubled wavelength is passed to become the probe beam 21b, and the undoubted part is reflected to become the pump beam 21a. The pump beam 21a is modulated by modulator 90 and is directed at normal incidence onto the sample 51 through objective 98. The probe beam polarization is rotated by means of a half wave plate 38 and is then passed through a polarizer 42 oriented to be orthogonal to the pump beam polarization. This retarder/polarizer combination is also used as a variable attenuator for the probe beam 21b. The probe beam 21b is then sent to the variable delay stage 44, and is focused onto the sample 51 through the same normal incidence objective 98 as the probe beam 21a. The reflected probe beam 21b' is directed to the detector 60 by a dichroic mirror 92 which passes the reflected pump beam 21a, thereby effectively filtering out any reflected probe light. A filter 94 which passes only the probe beam wavelength is placed before the detector 60. The detector 60 is followed by the tuned filter 62, lockin amplifier 64, and processor 66, as in FIG. 2.

Figure 7:
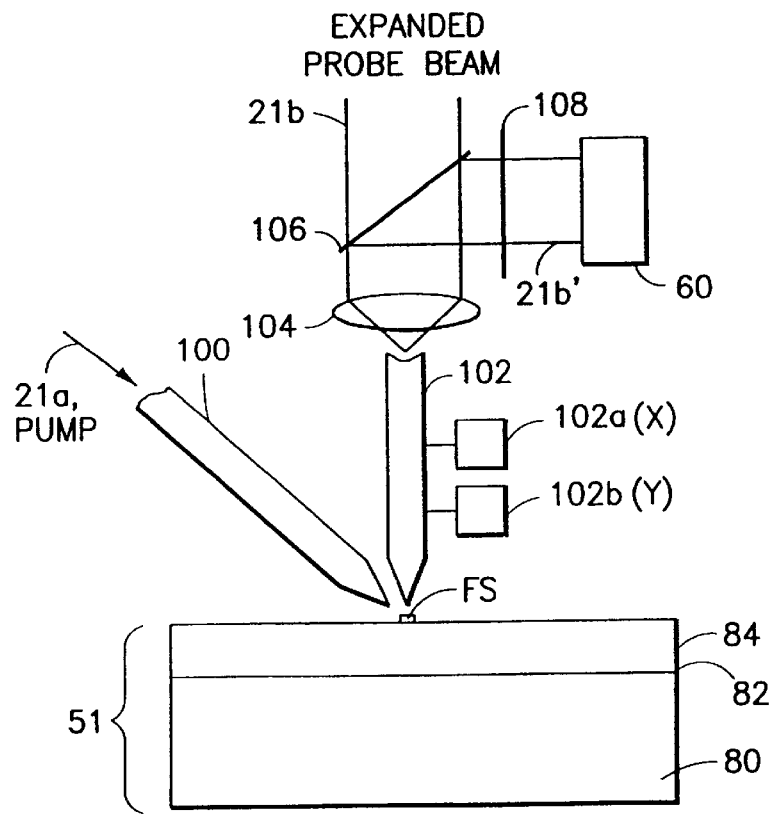
FIG. 7 illustrates a fiber optic-based pump and probe beam delivery and focussing system in accordance with an embodiment of this invention.

FIG. 7 illustrates an embodiment of this invention wherein the pump beam 21a and the probe beam 21b are directed to the sample 51 by means of tapered optical fibers 100 and 102, respectively, to achieve near-field focusing and FS sizes of order 100 nm. The probe beam 21b is shown having normal incidence, and may have a different wavelength than the pump beam 21a. In this embodiment a terminal portion of the pump and/or probe beam delivery fiber 100, 102 is reduced in diameter, such as by stretching the fiber, so as to provide a focussed spot FS having a diameter that is less than the normal range of optical focussing. This enables the pump and/or probe optical pulse to be repeatably delivered to a very small region of the sample's surface (e.g., to a spot having a diameter≦one micrometer), regardless of any changes that are occurring in the optical path length of the pump and/or probe beam.

The pump beam 21a need not be brought in through a fiber, and in one mode of operation may be much larger than the probe spot size on the sample. The probe beam 21b may then be scanned by x-axis and y-axis piezoelectric actuators 102a and 102b on a very small spatial scale (similar to a scanning Tunneling Microscope) with the pump beam location fixed. This embodiment may be used to map structures patterned in two or more dimensions on a length scale smaller than can be achieved using conventional lithography. Therefore, it can be used to map the smallest structures found in integrated circuits.

The probe beam 21b can be an expanded beam that is focused onto the fiber 102 by a lens 104, and the reflected probe beam 21b' is directed through the fiber 102 and is diverted by a splitter 106 to a filter 108 and then to the detector 60.

Figure 12:
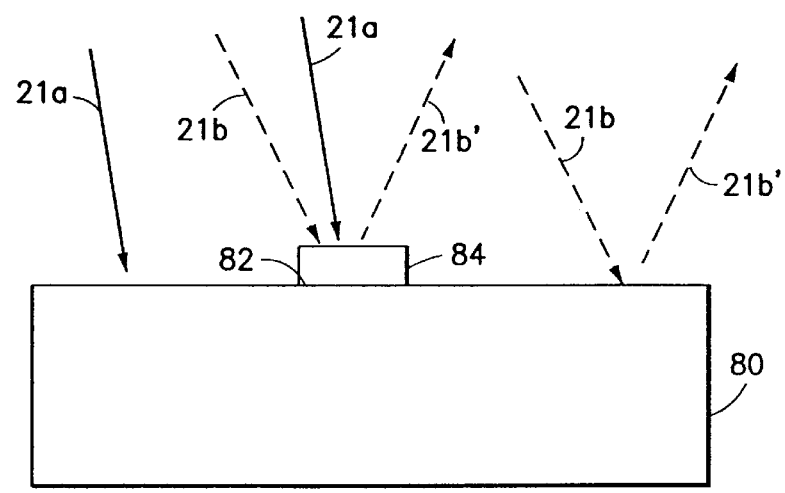
FIG. 12 is a cross-sectional, enlarged view of the sample having the substrate, a localized thin film structure disposed on a surface of the substrate, and the interface between the substrate and the thin film structure, and that further illustrates various methods to apply the pump and probe beams.

FIG. 12 shows an interface 82 between a patterned structure 84 on top of the substrate 80, and is useful in explaining the use of this invention when characterizing three dimensional structures as opposed to planar structures. The patterned structure may be evaluated by generating a stress wave in the substrate 80 and detecting the stress wave in the structure 84; or by generating the stress wave in the structure 84 and detecting the stress wave in the structure 84; or by generating the stress wave in the structure 84 and detecting the stress wave in the substrate 80.

Figure 13:
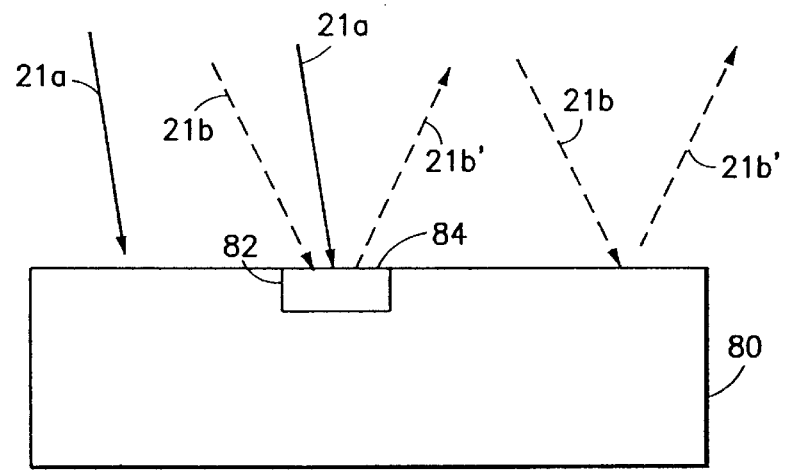
FIG. 13 is a cross-sectional, enlarged view of the sample having the substrate, a localized thin film structure disposed within a surface of the substrate, and the interface between the substrate and the thin film structure, and that further illustrates various methods to apply the pump and probe beams.

FIG. 13 shows an interface 82 surrounding a structure 84 formed within a patterned recess within a surface of substrate 80. An example of this three dimensional configuration is a tungsten via formed in a hole in a glass layer by (i) depositing the glass on a substrate, (ii) patterning and etching the hole, (iii) depositing a film of tungsten and (iv) polishing the tungsten layer until the glass is exposed (adhesion promoting layers may be deposited before the tungsten). The structure may be valuated by generating the stress wave in the substrate 80 (not applicable if the substrate, as in the above tungsten example, is glass) and detecting it in the embedded structure 84; or by generating the stress wave in the structure 84 and detecting the stress wave in the structure 84; or by generating the stress wave in the structure 84 and detecting the stress wave in the substrate 80.

It should be realized that, in the three dimensional structures illustrated in FIGS. 12 and 13, the pump beam can also be employed to excite the normal modes in the structure, which can in turn affect the transmitted or reflected probe beam.

When applying the probe beam 21b to the structure 84 it may be advantageous to use a near-field focussing arrangement, such as the tapered optical fiber shown in FIG. 7. In this case the pump beam FS can be significantly larger than the probe beam FS, thereby enabling the selective probing of small scale structures.

This capability for spatial imaging can be exploited to perform measurements of static stress with lateral spatial resolution to 100 nm scale and below.

It is also within the scope of this invention to apply a pump beam FS and a probe beam FS to simultaneously probe a plurality of patterned structures (e.g., a two-dimensional array of tungsten vias 0.5 $\mu$m in diameter and 1.0 $\mu$m apart that are formed in a substrate). In this case each tungsten via may be considered a separate, independent oscillator, each of which contributes to the reflected or transmitted probe beam signal. For closer spacings between elements, a "superlattice"-type of vibrational mode can be excited, wherein the reflected or transmitted probe signal includes coupling effects between the vias. In either case the probe beam signal can be compared to a signal obtained from a reference "known good" structure, or to a simulation of the structure, or from a combination of reference data and simulations. Any deviation in the probe signal from the reference and/or simulated signal may indicate that the sample differs in some way from what was expected.

Figure 14:
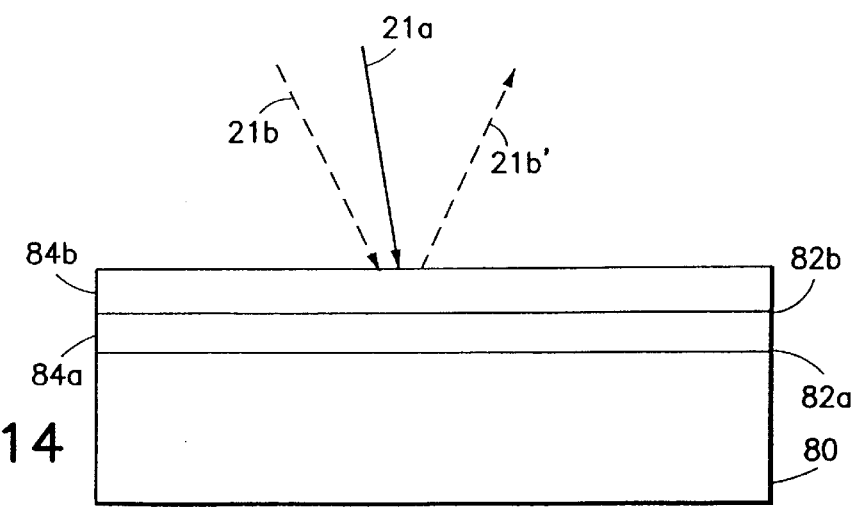
FIG. 14 is a cross-sectional, enlarged view of a sample having a substrate, a plurality of thin film layers, and interfaces between the substrate and one of the thin film layers and between the thin film layers.

FIG. 14 shows that for samples considered in the ultrasonic technique, a multilayer thin film 84a, 84b may be substituted for a simple film 84. Such multilayer films may be formed intentionally by sequential depositions, or unintentionally because the substrate 80 may have been ineffectively cleaned prior to succeeding layer depositions, or by the (intentional or unintentional) chemical reaction between two or more layers (for example, following heat treatment). Such layers may give rise to ultrasonic echoes having complicated shapes and temporal characteristics. It is possible to determine the thicknesses and interface characteristics for thin film structures containing, by example, five or more sublayers. This is preferably accomplished by comparing the reflectivity or transmission data with simulations of the ultrasonics and detection physics to obtain a best fit set of unknowns with the obtained data.

In the system configurations which use the AOM 40 to modulate the pump beam 21a, there may be no relationship between the modulation rate and the repetition rate of the laser 12. As a result, the laser pulse train and modulation cycle are asynchronous. It is possible to make this a synchronous system by deriving the modulation rate from the pulse repetition rate. The pulse repetition rate may be obtained from the laser 12 by means of an optical detector which senses the emitted pulses, or by using the drive signal from an actively mode-locked laser. To derive the modulation signal, the pulse rate signal is applied to a counter which changes the state of the modulator 40 after n laser pulses are counted. The modulation rate is then ½n times the laser pulse rate. In such a synchronous scheme the number of pump pulses impinging on the sample 51 in any period of the modulator 40 is always the same. This eliminates a potential source of noise in the modulated probe beam 21b which might arise in an asynchronous system under conditions in which the laser energy contained within a single cycle of the modulator 40 varies from period to period of the modulation.

A major source of noise is scattered pump light which can reach the probe beam detector (a) despite having a nominally orthogonal polarization (polarizers are not perfect, and also the sample 51 may tend to depolarize the light). As was described above, one technique to suppress this source of noise is to use pump and probe beams of different color, so that the pump color may be blocked by means of a filter before the probe detector.

Another method is to modulate the probe beam 21b at a frequency different from the pump beam modulation frequency. By example, if the pump modulation frequency is $f_1$ and the probe modulation frequency is $f_2$, then the part of the probe beam modulated by the pump beam at the sample 51 will have a component at the frequency $f_1-f_2$. This signal may be passed through a synchronous demodulator or low pass filter designed to reject $f_1$ and $f_2$ and pass only their difference frequency. Thus, any pump light scattered by the sample 51 onto the probe detector (a), which would otherwise appear as noise in the data, is suppressed. To minimize the introduction of ubiquitous 1/f noise the difference frequency is preferably not below a few hundred kHz. Exemplary frequencies are $f_1=1$ MHz and $f_2=500$ kHz.

For a sample 51 with the property that the incident light penetrates at least one wavelength into a layer or layers into which a stress wave is launched, it is possible to use picosecond ultrasonics to independently measure the sound velocity and refractive index of said layer or layers with great precision. The sound velocity may also be used to determine the elastic modulus. Optical interference between probe light reflected from the surface of the sample and probe light reflected from the traveling stress wave gives rise to oscillations in the intensity of the reflected probe beam $21b'$ as a function of delay. The period of these oscillations may be measured very precisely. For a material having an index of refraction n and sound velocity $v_s$ the period of the oscillations is given by:

$$\tau = \frac{\lambda_0}{2nv_s\cos\theta} \quad (2)$$

where $\lambda_0$ is the optical wavelength in free space and $\theta$ is the angle between the direction normal to the surface of the sample 51 and the direction of light propagation in the sample. Typically one knows $\theta$ and $\lambda_0$ in advance. Thus, from the observed oscillation period, one can deduce the product $nv_s$ with high precision. The value of $v_s$ independent of n can be found by measuring $\tau$ at a second angle (which yields a value for n), or by using a published value for n. In addition, from the sound velocity, the elastic modulus $c_{11} = \rho v_s^2$ of the film may be determined (using a previously determined value of $\rho$).

In accordance with an aspect of this invention measurements at two angles are simultaneously made by detecting parts of the probe beam $21b$ impinging on the sample 51 within a single focused beam, which then reflects to two or more closely spaced detectors. It is also within the scope of the invention to controllably tilt the sample stage 50, and to thus cause the probe beam $21b$ to impinge on the surface of the sample 51 at two or more different angles of incidence.

An alternative technique for determining n and $v_s$ has been described by Grahn et al. (APL 53, no. 21 (Nov. 21, 1988), pp. 2023–2024, and APL. 53, no. 23, Dec. 5, 1988), pp. 2281–2283). However, the Grahn et al. technique depends on the use of an independently-determined thickness for the film.

Representative samples for which these techniques may be used are illustrated in FIGS. 15a–15d.

In FIG. 15a a stress pulse is launched from the film layer 84 by the absorption of the pump beam energy, and propagates within the substrate 80 with a characteristic velocity $v_s$. The application of the probe beam pulse $21b$ results in two reflections, one from the surface of the film 84 and another from the stress pulse. As the stress pulse continues to propagate away from the film layer 84, the part of the probe pulse reflected at the stress wave has a changing phase shift relative to the probe pulse reflecting from the film's surface. One result is that constructive and destructive interference occurs between the probe pulse reflected from the surface and that reflected from stress wave, thereby giving a variation in the intensity of the probe pulse measured by the detectors as the stress pulse propagates.

In FIG. 15b the pump pulse launches the stress pulse either by being applied to the film surface or to the lower surface of the non-absorbing substrate 80. For the latter case the pump pulse propagates through the substrate 80 and is absorbed in the film 84, thereby generating the stress pulse. In either case the probe pulse is applied to the lower surface of the substrate 80, and gives rise to three temporally separated reflected probe beams $21b'$.

In FIG. 15c the substrate 80 is assumed to at least weakly absorb the pump pulse, giving rise to the stress pulse in the substrate. By example, the substrate 80 may be comprised of silicon.

In FIG. 15d a buried film 84 absorbs the pump pulse and launches a stress pulse that propagates towards the surface of an overlying transparent film $84'$. The resulting reflected probe pulses $21b'$ are similar to the case shown in FIG. 21b.

It should be noted that the teachings of this invention apply as well to very thin films that essentially vibrate when excited rather than supporting propagating stress or sound pulses.

In accordance with an interface characterization technique of this invention, amplitude information (i.e., the amplitude of the change in the reflected or transmitted probe beam intensity) is used to draw quantitative conclusions about the condition of buried interfaces or surfaces. The technique has superior sensitivity, compared to conventional ultrasonic techniques, to very subtle interfacial defects (contaminants, interlayers, roughness, bonding, etc.) because the wavelengths of the acoustic phonon comprising the pulse are much shorter than wavelengths which can be achieved by other methods. For example, in cases where distinct acoustic echoes are seen (e.g., for films thicker than few optical absorption lengths, and thin enough for an acoustic wave to return to the surface before the delay stage 44 runs out of delay travel), the echo amplitudes and widths can supply information about the smoothness of a buried interface from which it has reflected (see, for example, FIG. 15d).

An important mechanism determining such distortion of echo shapes is dephasing at different parts of the stress front reaching a roughened interface (and reflecting toward the surface) at different times. By incorporating such mechanisms into a simulation of a particular structure, it is possible to quantify the degree of interface roughness.

As employed herein the roughness of a surface or interlayer may be taken to be the RMS height and correlation length parallel to the surface or interlayer.

It should be noted that the same mechanism can cause echo broadening if it is the top surface (rather than a buried interface) which is rough. It is thus believed to be possible to distinguish between surface roughness-induced echo broadening and interface roughness-induced echo broadening based, for example, on the symmetry of the echoes and a comparison with reference echo shapes and/or simulated echo shapes.

It should be noted that the use of echoes per se is but one exemplary technique for characterizing the sample 51. For example, in some samples distinct echoes are not seen. However, the characterization of the sample can still be accomplished by comparing the reflected probe signal to reference data and/or simulations.

It is also within the scope of the teaching of this invention to detect roughness, or to detect variations in film thickness over small lateral displacements, through the use of a small area optical generator and detector which are scanned relative to the sample surface.

Interfacial layers are another potential cause of echo distortion. As in the preceding example, a preferred method to characterize such interfacial layers is to include them in a model of the sample structure (e.g. as a distinct film having certain physical properties, some of which may be of interest, and so may be left as fitting parameters).

In this regard it should be noted that Tas et al. reported detecting thin interfacial layers of $CF_x$ between aluminum and silicon as a particular example of this effect for a situation in which the aluminum films were very thin (G. Tas et al., Appl. Phys. Lett. 61(15), Oct. 12, 1992, pp. 1787–1789). Tas et al. did not observe echoes, but rather the ringing of the aluminum films. Moreover the result was for a very narrow class of structures in which the metal films were deposited on top of highly uniform, ultra thin layers of very soft material.

Interfacial layers producing much different effects can also be characterized with the technique of this invention.

An important class of interfacial layers include layers which are formed at interfaces between two materials which have chemically reacted to form an intermediate compound. As an example, Ti and Al react to form $TiAl_3$; Ti and Si react to form $TiSi_2$; Co and Si react to form $CoSi_2$; Pt and Si react to form PtSi. The thickness of interfacial layers so formed may be substantial. By example, in some of the above example pairings the materials may proceed until one or both of the original materials is completely consumed by the reaction.

Interfacial voids, cracks, and regions of poor adhesion may be detected similarly. Such defects usually give rise to acoustic reflections, such as but not limited to echoes, having larger amplitudes than would be seen for a perfect interface. The reason is that stress pulses exhibit no loss of amplitude when reflected from a perfectly free surface. As such, the presence of larger than expected probe signal amplitudes within the data can be indicative of, by example, a delamination between the film 84 and an underlying film or substrate.

This technique is also sensitive to thin film processes that are intended to enhance adhesion between layers. One such technique is ion bombardment. It has been found by the inventors that the rate of damping of ultrasonic ringing of a film deposited on a substrate, and then implanted with high energy ions, is more slowly damped for low ion doses than for high ion doses. It is inferred that the adhesion is greater for samples with higher implant doses because the acoustic energy in the thin film is able to couple to the substrate more readily than in samples having lower implant doses or energies.

In summary, an ultra short laser pulse ($\tau_p \sim 0.1$ psec) is selectively absorbed in a thin film or in a more complex nanostructure. The absorption sets up a thermal stress which generates an ultra short stress wave impulse. The propagating stress can affect the optical constants anywhere within the sample, causing a complex, but calculable, change in the reflectivity (or transmission, or polarization state, or optical phase) of the probe beam. Echoes are but one simple case of temporal features. Other, more complex temporal features may also be detected, such as those that correspond to ultrasonic vibrations in nanostructures and multilayer samples. These other temporal features may not correspond to a stress pulse returning to the surface. The only requirement for detection is that the stress generated by the pump is at a depth in the sample where it can interact with the probe beam.

A film or a multilayer deposited on a substrate at an elevated temperature is normally in a state of stress due to differential thermal expansion. Present techniques for evaluating the stress have severe practical limitations.

Measurements on several materials have shown how the temperature dependence $\partial v_s/\partial T$ of the sound velocity is affected by stress. This quantity can be readily measured by the picosecond ultrasonic methods of this invention and can be used to give the stress of the film, without the requirement of knowing the film's precise thickness. The technique has many advantages and is applicable even for very thin films, multilayers (~100 Å), and for submicron lateral dimensions.

Further in accordance with this invention, the sound velocity in a film is measured at two temperatures in the film. The difference between the two sound velocities depends in a predictable way on the stress within the film, whether the stress is externally imposed or "built-in". This provides a method for stress measurement on a lateral scale of the spot size FS, which may have a diameter of one micron or less. The temperature of the sample 51 can be changed via a resistively heated stage, an arc lamp, a CW laser focused onto the measurement spot, or by modulating the pump power. The sound velocity can be measured by observing ultrasonic echoes, or oscillatory signals as disclosed in regard to FIGS. 15a–15d, or the vibrational period of very thin films.

The rate of change of the sound velocity with temperature depends on the stress in the film in a predictable way, as has been reported in the literature (Salama K. et al., Journal of Applied Physics vol. 51, page 1505 et seq. (1980); J. Cantrell, Ultrasonics International 1989 Conference Proceedings, pp. 977 et seq.).

Picosecond ultrasonics measurements of the sound velocity may be made in the following ways: echo time (as in Tauc et al.); ringing period; the oscillation period of oscillations caused by a travelling stress wave in semitransparent or transparent samples, or by producing a best fit to picosecond ultrasonic data by varying a sound velocity parameter in a simulation of one or more layers.

The temperature may be changed in the following ways: by a resistive heater embedded in the sample stage 50; by an inductive heater; radiatively (i.e. an intense lamp); by varying the pump beam intensity such that the mean temperature of the sample is above the ambient; or by introducing a continuous wave heating laser onto the measurement spot FS through a common or separate objective.

The temperature change may be measured in the following ways: by optical pyrometry; by a calculation of the deposited heating energy (which requires measurement of the incident and reflect radiation) and then using the values of the optical and thermal constants of the sample needed to determine the equilibrium temperature in the measurement region; with a thermocouple (in contact with the sample 51); or using the Mirage Effect. In the Mirage Effect the change in the refractive index in the air above the heated spot is measured via the deflection of a laser beam incident at a glancing angle, and the temperature is deduced from the refractive index change necessary to produce an observed beam deflection (see, for example, T. R. Anthony et al., Physical Review B, vol. 42, 1104 (1990)).

Calibration of the system of this invention can be accomplished in several manners. By example, films comprised of several different metals can be deposited on silicon wafers at different temperatures. In these samples, the stress can be independently estimated by calculation from differential expansion and from measurements of film-induced curvature. The calculated values are then compared with results obtained from the use of the system of this invention, and calibration factors are determined accordingly.

The teaching of this invention also includes methods and apparatus for measuring the change in the optical constants of a material with strain. In this technique the system is used to determine the quantities $\partial n/\partial \eta$ and $\partial \kappa/\partial \eta$ in a particular sample geometry. Samples have a film of glass, or another transparent material deposited on top of a thin film of opaque or semi-opaque material (the material of interest may be a metal). The optical constants of both materials are known. The quantities $\partial n/\partial \eta$ and $\partial \kappa/\partial \eta$ are also known for the transparent material, and are deduced for the second material by comparing acoustic data with simulations in which $\partial n/\partial \eta$ and $\partial \kappa/\partial \eta$ for the second material are varied.

To be able to carry out simulations which enable a quantitative comparison with data of the magnitude of the change in the reflectivity or transmissivity of a sample in which a stress pulse is generated, it is necessary to know in advance by how much the optical constant n and κ for the subject materials change in response to stress σ. It is preferable in some embodiments to carry out simulations in terms of the strain $\eta$, which may be related to the stress in a simple way. In terms of the strain, the foregoing is equivalent to the statement that the quantities $\partial n/\partial \eta$ and $\partial \kappa/\partial \eta$ must be known. It is a feature of this invention that the methods and apparatus described herein may be used to determine these quantities. In one technique, $\partial n/\partial \eta$ and $\partial \kappa/\partial \eta$ may be found for a material by depositing on top of an optically smooth specimen of this material a layer of transparent material such as a glass (e.g. LP-CVD TEOS, or PE-CVD BPSG) having a thickness of at least several hundred Angstroms, and less than 100 microns. The underlying specimen of material for which $\partial n/\partial \eta$ and $\partial \kappa/\partial \eta$ are to be determined may be a thin film, or a thick substrate. The process of determining $\partial n/\partial \eta$ and $\partial \kappa/\partial \eta$ involves two steps which may be described in relation to FIG. 15d (which shows the case in which the material of interest is a thin metal film disposed on top of a substrate which may be silicon. In step (1) a stress pulse is generated in the material. Part of this stress wave enters the transparent layer and propagates to the free surface, then reflects from this surface, then propagates through the transparent layer, and then part of this stress reenters the metal film. The stress pulse reflecting from the free surface has the opposite sign to the incident stress pulse, but identical amplitude. The fraction of the stress pulse incident from the glass layer on the metal film which reenters the metal film may be calculated from the acoustic impedances (i.e. the product of the sound velocity and density) of the glass and metal (as described in Tauc et al.). While the stress wave propagates through the glass layer it gives rise to oscillations as described previously with regard to FIGS. 15a–15d. The amplitude of these oscillations may be used to compute the quantity $\partial n/\partial \eta$ for the glass (which in general will have a different value than the. value corresponding to the metal) either analytically or by comparison with simulations of the oscillations: $\partial \kappa/\partial \eta = 0$ for the glass. In step (2) the quantities $\partial n/\partial \eta$ and $\partial \kappa/\partial \eta$ for the metal layer are determined by carrying out a simulation of the reflectivity change which occurs in response to the stress reentering this layer, and by adjusting $\partial n/\partial \eta$ and $\partial \kappa/\partial \eta$ in order to achieve a best fit to the observed response for times during which the effects of the stress wave on the reflected probe intensity may be observed. In these simulations the acoustic impedances and sound velocities of the glass and metal film are assumed to be known in advance. In addition, the optical constants n and $\kappa$ for one or both materials at the pump and probe beam wavelengths may be used as inputs to the simulations, or alternatively may be used as further adjustable parameters.

An important feature of this procedure is that simulation parameters so determined should simultaneously fit the response corresponding to the stress wave propagating in the metal. In the above procedure it is assumed that the detector 60 and processor 66 are so calibrated as to give the true reflectivity of the sample as a function of time. An alternative three step procedure which does not require the detector 60 and processor 66 to be so calibrated is as follows. In step (1) a stress pulse is generated in the material. Part of this stress wave enters the transparent layer and propagates to the free surface, then reflects from this surface, then propagates through the transparent layer, and then part of this stress reenters the metal film. The stress pulse reflecting from the free surface has the opposite sign to the incident stress pulse, but identical amplitude. The fraction of the stress pulse incident from the glass layer on the metal film which reenters the metal film may be calculated from the acoustic impedances (i.e. the product of the sound velocity and density) of the glass and metal (as described in Tauc et al). While it propagates through the glass layer the stress wave gives rise to oscillations as described previously with regard to FIGS. 15a–15d. In step (2) $\partial n/\partial \eta$ for the glass and $\partial n/\partial \eta$ and $\partial \kappa/\partial \eta$ for the metal are allowed to be freely varied in the simulated response in order to achieve a best fit to the observed response. The values $\partial n/\partial \eta$ and $\partial \kappa/\partial \eta$0 obtained may be scaled by the ratio of the true value of $\partial n/\partial \eta$ for the glass to the fitted value. Therefore, in Step (3) the true value of $\partial n/\partial \eta$ for the glass is determined (this may be obtained by a number of methods, other than picosecond ultrasonics, that are applicable to transparent materials), and the fitted $\partial n/\partial \eta$ and $\partial \kappa/\partial \eta$ for the metal are scaled to obtain their true values.

It is also within the scope of the teaching of this invention to use the derivative of the signal versus time to determine the properties of a sample, rather than the signal itself. The purpose is to remove some of the background signal, associated with the cooling of the film, from the data. The derivative of the signal can also be compared with the derivative of a simulation to extract parameters.

In one embodiment of the algorithm used to determine unknown quantities from the observed reflectivity or transmission of the sample, the temporal features associated with the propagation of stress within the sample are compared with a simulation which includes only the ultrasonic response. Other features, in particular the slowly varying background associated with diffusion of heat within the sample, are ignored in such comparisons, or may be included in the fitting process by introducing one or several fitting parameters of a slowly varying function (e.g. an exponential, or a low order polynomial). For some materials the slowly varying background may have a much greater amplitude than the features associated with ultrasonic response of the sample. In order to improve the accuracy and speed of the fitting process in such situations, it may be convenient to numerically compute the derivative of the response with respect to delay time. A comparison may then be made between the derivative so determined and the derivative of the simulated response, and the values of the unknowns varied until a best fit is obtained.

An alternative method is to measure the derivative of the sample response directly, avoiding the step of numerical differentiation. This method provides superior signal to noise in comparison to the numerical procedure. In one embodiment of this derivative measurement scheme the retroreflector 46 in the probe path is placed on a mount (such as a piezoelectric actuator) which is caused to oscillate rapidly ($f_2$) (i.e. from 10 to $10^6$ Hz) along the probe beam axis, thus executing a large number of oscillations (i.e., greater than 10) for each successive delay position of the delay mechanism. The signal measured in such a system may be related to the derivative of the signal versus delay by a simple proportionality constant, provided that the amplitude of the oscillations corresponds to a range of delays which are small compared to the minimum temporal extent of observed ultrasonic features in an undifferentiated response. In this embodiment it is also possible to detect at the difference frequency ($f_1-f_2$ or $f_1+f_2$), where $f_1$ is the frequency induced by the AOM in the pump beam path (e.g., 1 MHz), and $f_2$ is the frequency induced by the delay modulator in the probe beam path.

Figure 16:
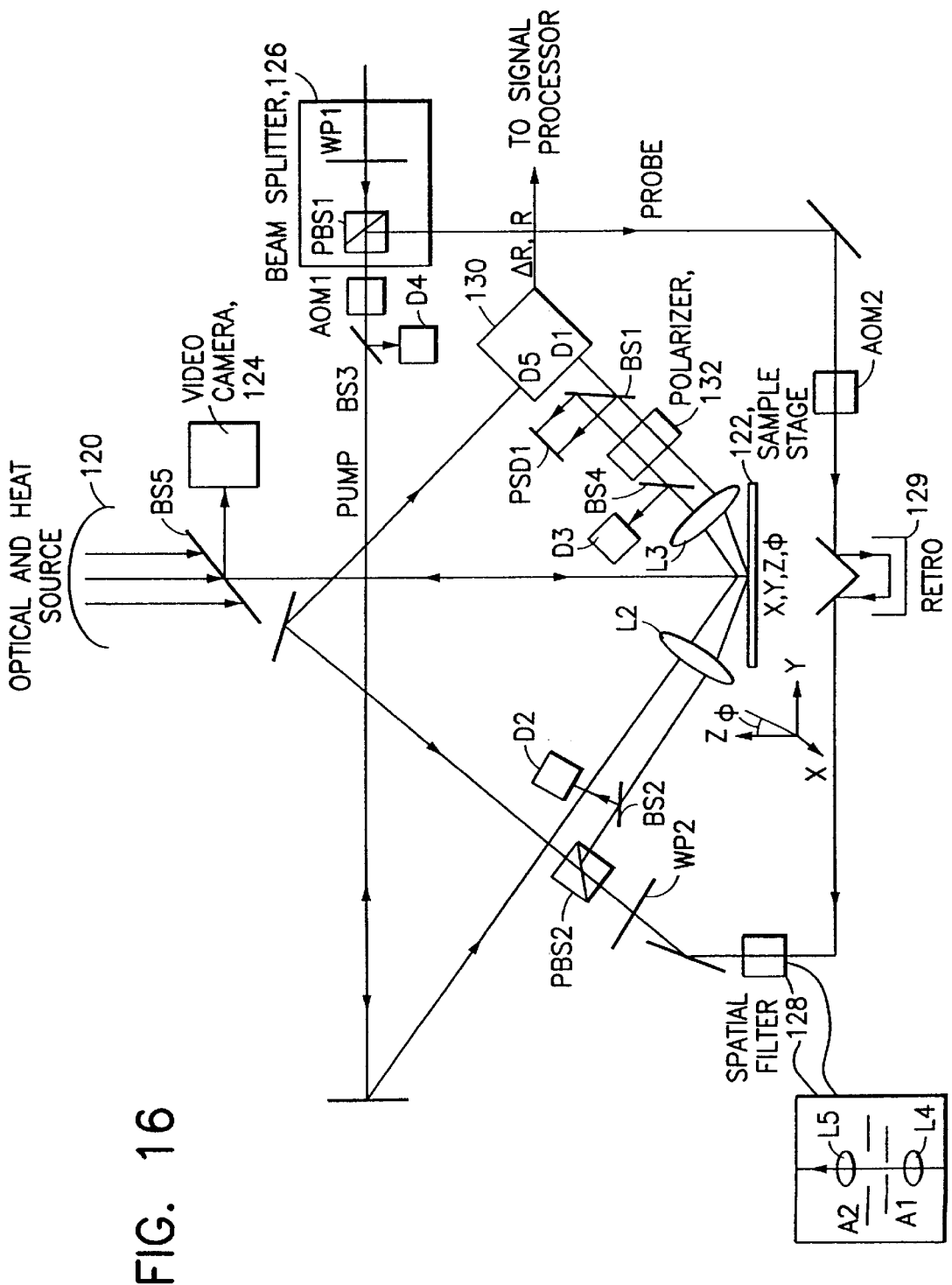
FIG. 16 is a block diagram of a first embodiment of a picosecond ultrasonic system in accordance with this invention, specifically, a parallel, oblique beam embodiment.

Reference is now made to FIG. 16 for illustrating an embodiment of this invention which is referred to as a parallel, oblique embodiment.

This embodiment includes an optical/heat source 120, which functions as a variable high density illuminator, and which provides illumination for a video camera 124 and a sample heat source for temperature-dependent measurements under computer control. An alternative heating method employs a resistive heater embedded in the stage sample stage 122. The advantage of the optical heater is that it makes possible rapid sequential measurements at two different temperatures, as will be described below. The video camera 124 provides a displayed image for an operator, and facilitates the set-up of the measurement system. Appropriate pattern recognition software can also be used for this purpose, thereby minimizing or eliminating operator involvement.

The sample stage 122 is preferably a multiple-degree of freedom stage that is adjustable in height (z-axis), position (x and y-axes), and tilt (Θ), and allows motor controlled positioning of a portion of the sample relative to the pump and probe beams. The z-axis is used to translate the sample vertically into the focus region of the pump and probe, the x and y-axes translate the sample parallel to the focal plane, and the tilt axes adjust the orientation of the stage 122 to establish a desired angle of incidence for the probe beam. This is achieved via detectors PDS1 and PDS2 and the local processor, as described below.

In an alternative embodiment, the optical head may be moved relative to a stationary, tiltable stage 122' (not shown). This is particularly important for scanning large objects (such as 300 mm diameter wafers, or mechanical structures, etc.) In this embodiment the pump beam, probe beam, and video are delivered to the translatable head via optical fibers or fiber bundles.

BS5 is a broad band beam splitter that directs video and a small amount of laser light to the video camera 124. The camera 124 and local processor can be used to automatically position the pump and probe beams on a measurement site.

The pump-probe beam splitter 126 splits an incident laser beam pulse (preferably of picosecond or shorter duration) into pump and probe beams, and includes a rotatable half-wave plate (WPI) that rotates the polarization of the unsplit beam. WP1 is used in combination with polarizing beam splitter PBS1 to effect a continuously variable split between pump and probe power. This split may be controlled by the computer by means of a motor to achieve an optimal signal to noise ratio for a particular sample. The appropriate split depend on factors such as the reflectivity and roughness of the sample. Adjustment is effected by having a motorized mount rotate WP1 under computer control.

A first acousto-optic modulator (AOM1) chops the pump beam at a frequency of about 1 MHz. A second acousto-optic modulator (AOM2) chops the probe beam at a frequency that differs by a small amount from that of the pump modulator AOM1. The use of AOM2 is optional in the system illustrated in FIG. 16. As will be discussed below, the AOMs may be synchronized to a common clock source, and may further be synchronized to the pulse repetition rate (PRR) of the laser that generates the pump and probe beams.

A spatial filter 128 is used to preserve at its output a substantially invariant probe beam profile, diameter, and propagation direction for an input probe beam which may vary due to the action of the mechanical delay line shown as the retroreflector 129. The spatial filter 128 includes a pair of apertures A1 and A2, and a pair of lenses L4 and L5. An alternative embodiment of the spatial filter incorporates an optical fiber, as described above.

WP2 is a second adjustable half wave plate which functions in a similar manner, with PBS2, to the WP1/PBS1 of the beamsplitter 126. With WP2 the intent is to vary the ratio of the part of the probe beam impinging on the sample to that of the portion of the beam used as a reference (input to D5 of the detector 130. WP2 may be motor controlled in order to achieve a ratio of approximately unity. The electrical signals produced by the beams are subtracted, leaving only the modulated part of the probe to be amplified and processed. PSD2 is used in conjunction with WP2 to achieve any desired ratio of the intensities of the probe beam and reference beam. The processor may adjust this ratio by making a rotation of WP2 prior to a measurement in order to achieve a nulling of the unmodulated part of the probe and reference beam. This allows the difference signal (the modulated part of the robe) alone to be amplified and passed to the electronics.

The beamsplitter BS2 is used to sample the intensity of the incident probe beam in combination with detector D2. The linear polarizer 132 is employed to block scattered pump light polarization, and to pass the probe beam. Lenses L2 and L3 are pump and probe beam focusing and collimating objectives respectively. The beamsplitter BS1 is used to direct a small part of pump and probe beams onto a first Position Sensitive Detector (PSD1) that is used for autofocusing, in conjunction with the processor and movements of the sample stage 122. The PSD1 is employed in combination with the processor and the computer-controlled stage 122 (tilt and z-axis) to automatically focus the pump and probe beams onto the sample to achieve a desired focusing condition.

The detector D1 may be used in common with acoustics, ellipsometry and reflectometry embodiments of this invention. However, the resultant signal processing is different for each application. For acoustics, the DC component of the signal is suppressed such as by subtracting reference beam input D5, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of the rotation compensator (see FIG. 17), and the resulting waveform is analyzed to yield the ellipsometric parameters. For reflectometry, the change in the intensity of the entire unmodulated probe beam due to the sample is determined by using the D1 and D2 output signals (D2 measures a signal proportional to the intensity of the incident probe). Similarly, additional reflectometry data can be obtained from the pump beam using detectors D3 and D4. The analysis of the reflectometry data from either or both beams may be used to characterize the sample. The use of two beams is useful for improving resolution, and for resolving any ambiguities in the solution of the relevant equations.

A third beamsplitter BS3 is used to direct a small fraction of the pump beam onto detector D4, which measures a signal proportional to the incident pump intensity. A fourth beamsplitter BS4 is positioned so as to direct a small fraction of the pump beam onto detector D3, which measures a signal proportional to the reflected pump intensity.

Figure 17:
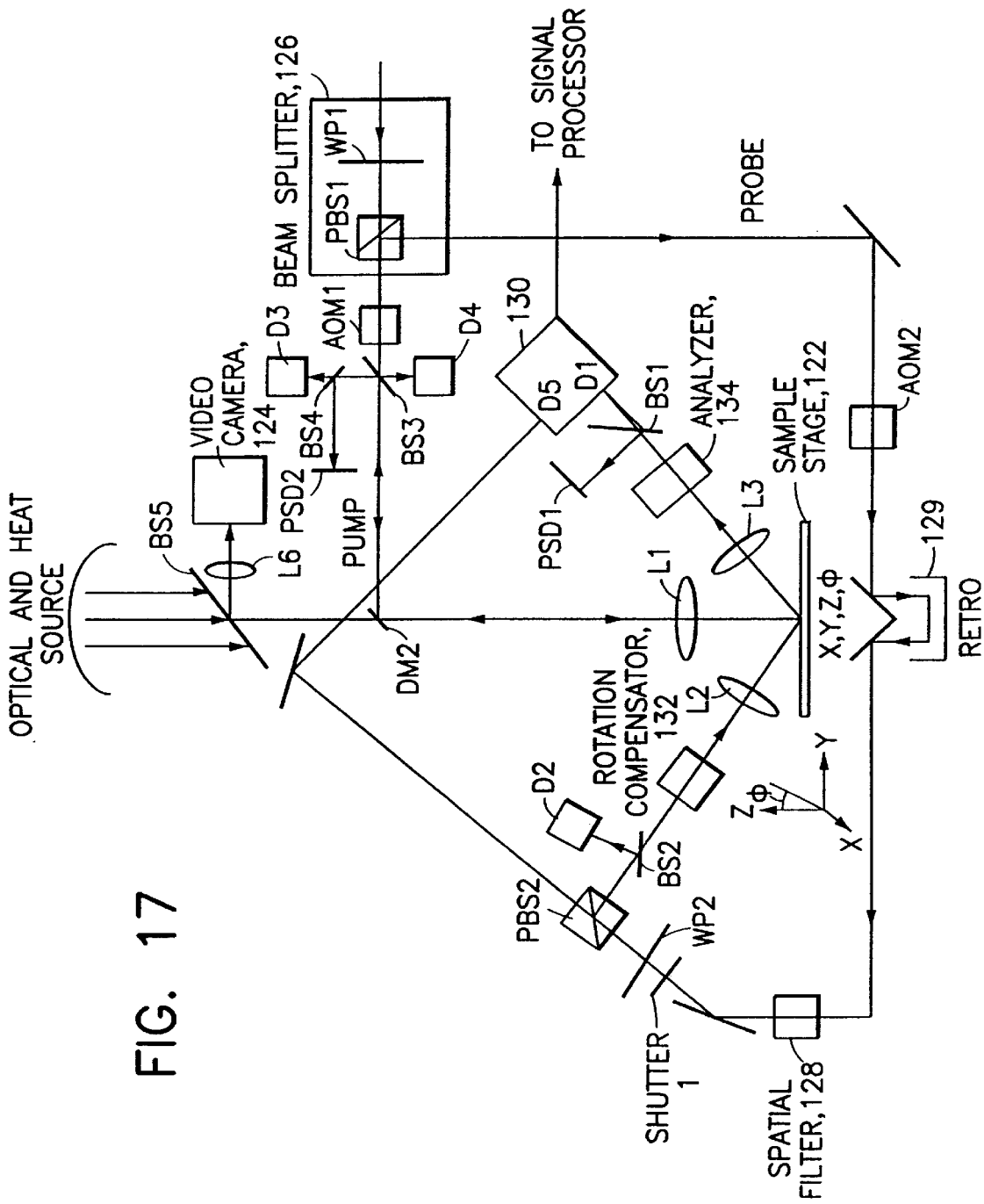
FIG. 17 is a block diagram of a second embodiment of a picosecond ultrasonic system in accordance with this invention, specifically, a normal pump, oblique probe embodiment.

FIG. 17 illustrates a normal pump beam, oblique probe beam embodiment of this invention. Components labelled as in FIG. 16 function in a similar manner, unless indicated differently below. In FIG. 17 there is provided the above-mentioned rotation compensator 132, embodied as a linear quarter wave plate on a motorized rotational mount, and which forms a portion of an ellipsometer mode of the system. The plate is rotated in the probe beam at a rate of, by example, a few tens of Hz to continuously vary the optical phase of the probe beam incident on the sample. The reflected light passes through an analyzer 134 and the intensity is measured and transferred to the processor many times during each rotation. The signals are analyzed according to known types of ellipsometry methods to determine the characteristics of the sample (transparent or semitransparent films). This allows the (pulsed) probe beam to be used to carry out ellipsometry measurements.

In accordance with an aspect of this invention the ellipsometry measurements are carried out using a pulsed laser, which is disadvantageous under normal conditions, since the bandwidth of the pulsed laser is much greater than that of a CW laser of a type normally employed for ellipsometry measurements.

When acoustics measurements are being made, the rotation compensator 132 is oriented such that the probe beam is linearly polarized orthogonal to the pump beam.

The analyzer 134 may be embodied as a fixed polarizer, and also forms a portion of the ellipsometer mode of the system. When the system is used for acoustics measurements the polarizer 134 is oriented to block the pump polarization. When used in the ellipsometer mode, the polarizer 134 is oriented so as to block light polarized at 45 degrees relative to the plane of the incident and reflected probe beam.

Finally, the embodiment of FIG. 17 further includes a dichroic mirror (DM2), which is highly reflective for light in a narrow band near the pump wavelength, and is substantially transparent for other wavelengths.

It should be noted in FIG. 17 that BS4 is moved to sample the pump beam in conjunction with BS3, and to reflect a portion of the pump to D3 and to a second PSD (PSD2). PSD2 (pump PSD) is employed in combination with the processor, computer controlled stage 122 (tilt and z-axis), and PSD1 (Probe PSD) to automatically focus the pump and probe beams onto the sample to achieve a desired focusing condition. Also, a lens L1 is employed as a pump, video, and optical heating focussing objective, while an optional lens L6 is used to focus the sampled light from BS5 onto the video camera 124.

Figure 18:
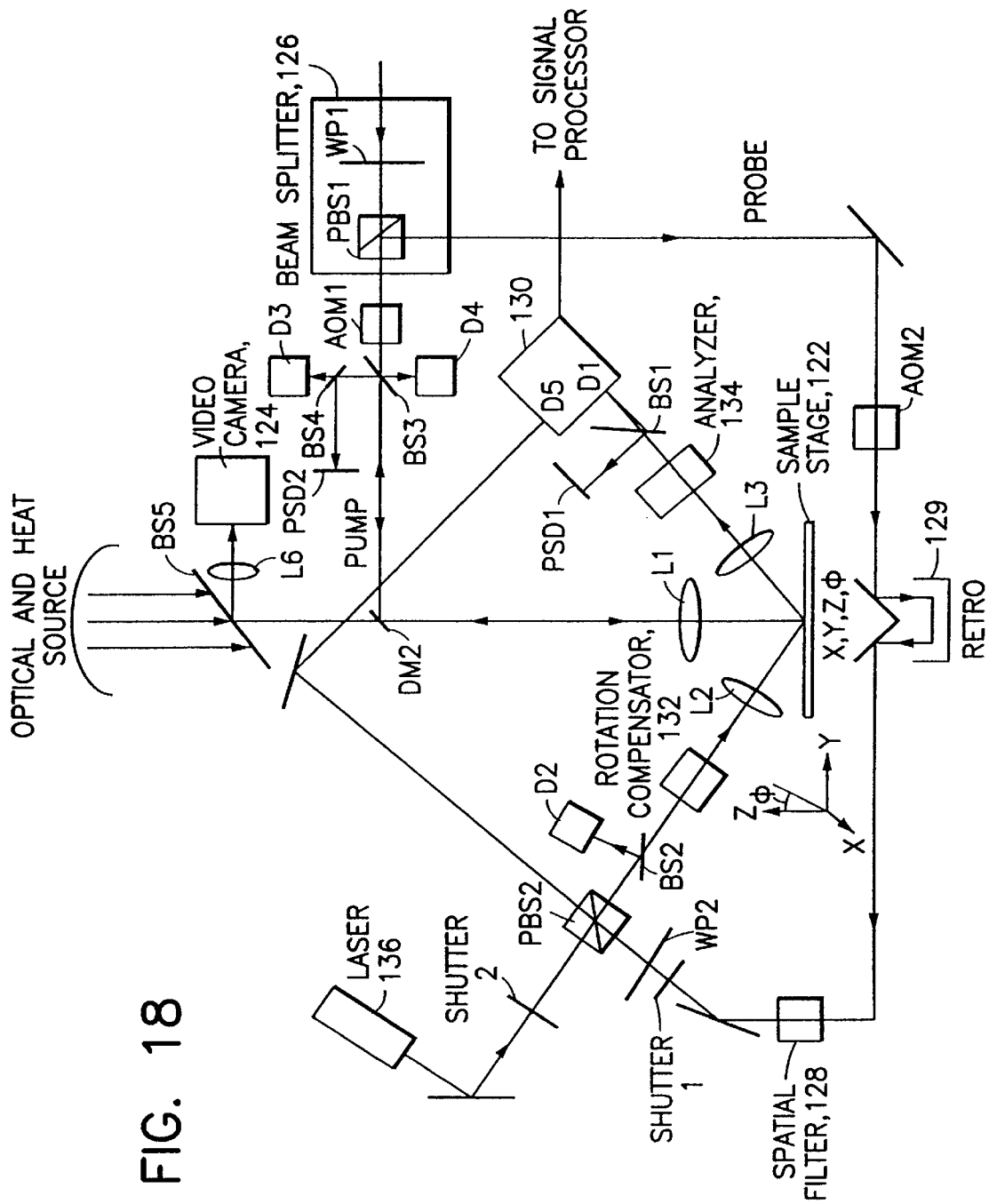
FIG. 18 is a block diagram of a third, presently preferred embodiment of a picosecond ultrasonic system in accordance with this invention, specifically, a single wavelength, normal pump, oblique probe, combined ellipsometer embodiment.

Reference is now made to FIG. 18 for illustrating a further embodiment of the picosecond ultrasonics system, specifically a single wavelength, normal pump, oblique probe, combined ellipsometer embodiment. As before, only those elements not described previously will be described below.

Shutter 1 and shutter 2 are computer controlled shutters, and allow the system to use a He—Ne laser 136 in the ellipsometer mode, instead of the pulsed probe beam. For acoustics measurements shutter 1 is open and shutter 2 is closed. For ellipsometer measurements shutter 1 is closed and shutter 2 is opened. The HeNe laser 136 is a low power CW laser, and has been found to yield superior ellipsometer performance for some films.

Figure 19:
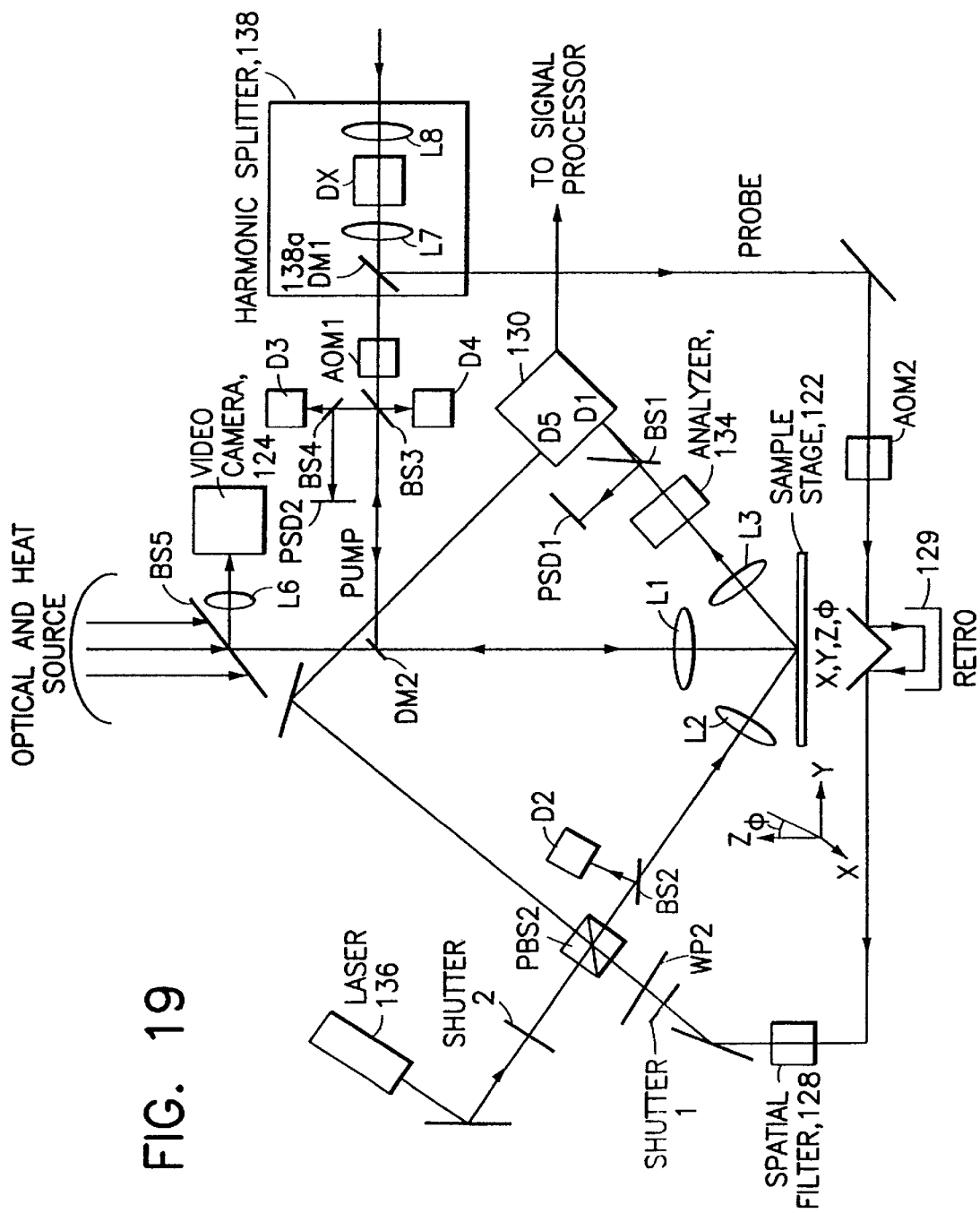
FIG. 19 is a block diagram of a fourth embodiment of a picosecond ultrasonic system in accordance with this invention, specifically, a dual wavelength, normal pump, oblique probe, combined ellipsometer embodiment.

FIG. 19 is a dual wavelength embodiment of the system illustrated in FIG. 18. In this embodiment the beamsplitter 126 is replaced by a harmonic splitter, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam is shown transmitted by the dichroic mirror (DM 138a) to the AOM1, while the probe beam is reflected to the retroreflector. The reverse situation is also possible. The shorter wavelength may be transmitted, and the longer wavelength may be reflected, or vice versa. In the simplest case the pump beam is the second harmonic of the probe beam (i.e., the pump beam has one half the wavelength of the probe beam).

It should be noted that in this embodiment the AOM2 is eliminated since rejection of the pump beam is effected by means of color filter F1, which is simpler and more cost effective than heterodying. F1 is a filter having high transmission for the probe beam and the He—Ne wavelengths, but very low transmission for the pump wavelength.

Figure 20:
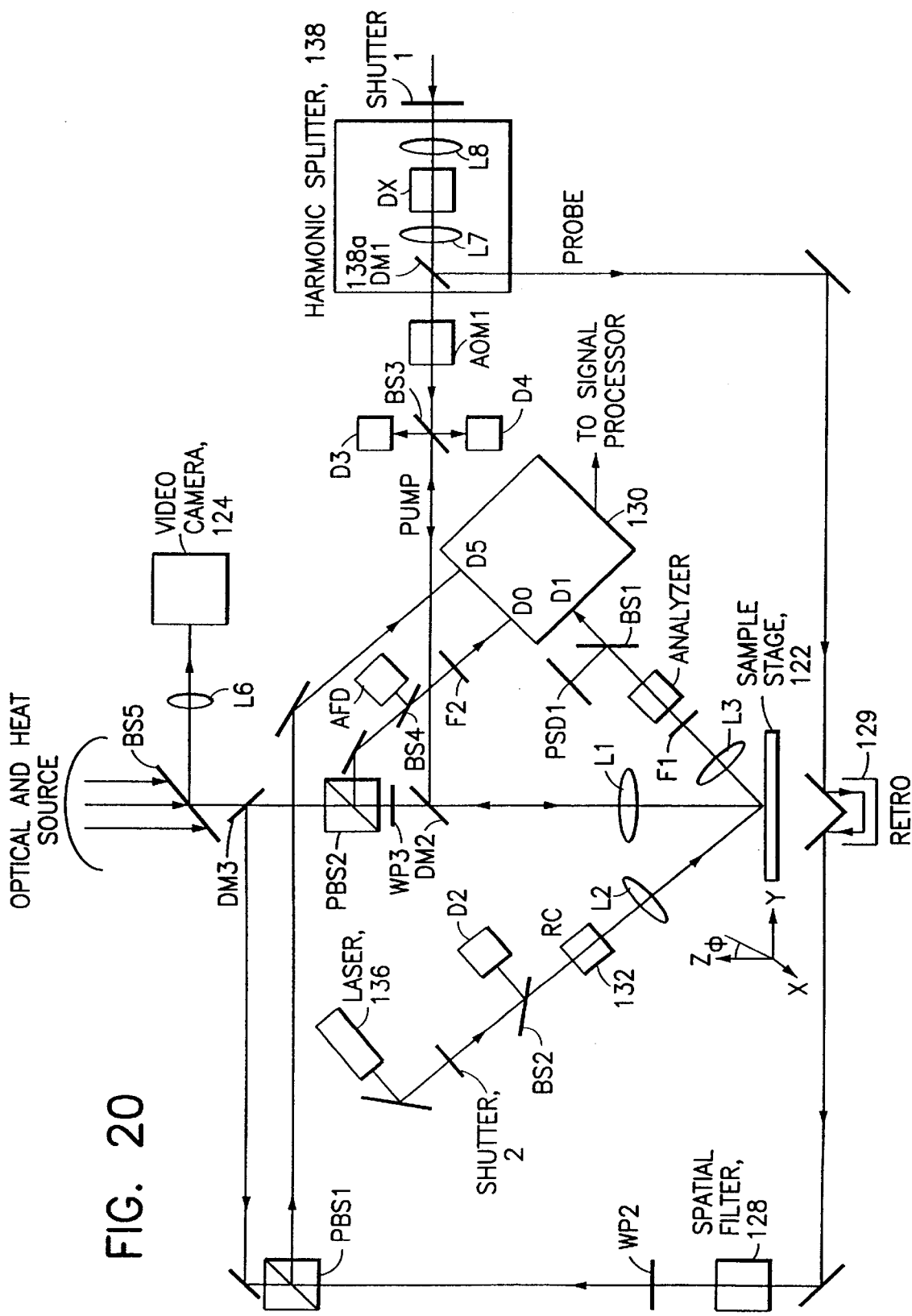
FIG. 20 is a block diagram of a fifth embodiment of a picosecond ultrasonic system in accordance with this invention, specifically, a dual wavelength, normal incidence pump and probe, combined ellipsometer embodiment.

Finally, FIG. 20 illustrates a normal incidence, dual wavelength, combined ellipsometer embodiment of this invention. In FIG. 20 the probe beam impinges on PBS2 and is polarized along the direction which is passed by the PBS2. After the probe beam passes through WP3, a quarter wave plate, and reflects from the sample, it returns to PBS2 polarized along the direction which is highly reflected, and is then directed to a detector D0 in detector block 130. D0 measures the reflected probe beam intensity.

In greater detail, WP3 causes the incoming plane polarized probe beam to become circularly polarized. The handedness of the polarization is reversed on reflection from the sample, and on emerging from WP3 after reflection, the probe beam is linearly polarized orthogonal to its original polarization. BS4 reflects a small fraction of the reflected probe onto an Autofocus Detector AFD.

DM3, a dichroic mirror, combines the probe beam onto a common axis with the illuminator and the pump beam. DM3 is highly reflective for the probe wavelength, and is substantially transparent at most other wavelengths.

D1, a reflected He—Ne laser 136 detector, is used only for ellipsometric measurements.

It should be noted that, when contrasting FIG. 20 to FIGS. 18 and 19, that the shutter 1 is relocated so as to intercept the incident laser beam prior to the harmonic splitter 138.

Based on the foregoing descriptions of a number of embodiments of this invention, it can be appreciated that this invention teaches, in one aspect, a picosecond ultrasonic system for the characterization of samples in which a short optical pulse (the pump beam) is directed to an area of the surface of the sample, and then a second light pulse (the probe beam) is directed to the same or an adjacent area at a later time. The retroreflector 129 shown in all of the illustrated embodiments 16–20 can be employed to provide a desired temporal separation of the pump and probe beams, as was described previously with regard to, by example, FIG. 9.

The system measures some or all of the following quantities: (1) the small modulated change $\Delta R$ in the intensity of the reflected probe beam, (2) the change $\Delta T$ in the intensity of the transmitted probe beam, (3) the change $\Delta P$ n the polarization of the reflected probe beam, (4) the charge $\Delta \phi$ in the optical phase of the reflected probe beam, and/or (5) the change in the angle of reflection $\Delta \delta$ of the probe beam. These quantities (1)–(5) may all be considered as transient responses of the sample which are induced by the pump pulse. These measurements can be made together with one or several of the following: (a) measurements of any or all of the quantities (1)–(5) just listed as a function of the incident angle of the pump or probe light, (b) measurements of any of the quantities (1)–(5) as a function of more than one wavelength for the pump and/or probe light, (c) measurements of the optical reflectivity through measurements of the incident and reflected average intensity of the pump and/or probe beams; (d) measurements of the average phase change of the pump and/or probe beams upon reflection; and/or (e) measurements of the average polarization and optical phase of the incident and reflected pump and/or probe beams. The quantities (c), (d) and (e) may be considered to be average or static responses of the sample to the pump beam.

One function of the system is to determine the thickness of the films making up the sample, the mechanical properties of the films (sound velocities and densities), and the characteristics of the interfaces (adhesion, roughness, and other interfacial characteristics).

The system in accordance with the various embodiments of this invention thus enables a combination of measurements of the type listed above so as to enable the determination of properties of the sample that are not obtainable through the use of conventional systems.

By example, consider a sample in which the upper-most film is transparent. In such a sample the pump pulse will not be absorbed in this film, but will instead be absorbed in the next underlying film, assuming that this film is not also transparent. There will, however, normally be a contribution to the change $\Delta R$ in reflectivity of the probe pulse from the uppermost transparent film. A stress wave will be generated in the underlying optically-absorbing film and will propagate into the transparent film. This will cause a local change $\Delta \eta$ in the refractive index n of the transparent film, and the location of this change in the refractive index will propagate towards the free surface of the transparent film with a speed equal to the sound velocity v in the film. Probe light which is reflected at this change in n will interfere constructively or destructively with the probe light which is reflected at the other interfaces of the sample. As a consequence there will be a change $\Delta R$ in the intensity of the reflected probe light, which change will amount to an oscillation of frequency f given by $$f = 2nv \cos\frac{\alpha}{\lambda}$$

where $\lambda$ is the wavelength in free space of the probe light and $\theta$ is the angle between the direction of the probe light in the sample and the normal to the surface. Hence a measurement of the frequency of this oscillation can be used to determine the product nv, but not n and v separately. This oscillation will suffer an abrupt change in phase when the stress pulse reaches the free surface of the sample at time $\tau_1$ and is then reflected back. By a measurement of $\tau_1$ one can thus determine the quantity d/v, where d is the film thickness. These two measurements and their analysis may be obtained using conventional systems, but do not lead to definite values for the three quantities of interest n, v, and d. The present invention overcomes this difficulty as follows.

If measurements are made of the frequency f as a function of the angle of incidence $\theta$ of the probe light outside the sample the measured $f(\theta)$ can be analyzed to give both n and v. This is because the relation between $\alpha$ and $\theta$ involves only n and not v. Then the measurement of the time $\tau_1$ can be used to determine d.

Second, using measurements of the intensity of the reflected pump or probe light, the phase change or the relative intensities of the different polarization components of the pump and/or probe light can also be used in many circumstances to deduce the refractive index and/or the thickness of the transparent film. For example, the thickness or optical constants of one or more layers in a sample may be determined from the measured quantities according to the principles of optical reflectometry or ellipsometry. In this case the picosecond light pulses available in the system of this invention can be used to make such reflectometry or ellipsometry measurements, and extra light sources may not be needed. The pulsed nature of the lasers is not relevant to these measurements. The determination of the optical constants and/or film thicknesses then enables the sound velocity and/or the thickness to be deduced from a single measurement of the frequency f.

The foregoing example has been described in terms of a measurement of $\Delta R(t)$; clearly the same technique may be applied to the other transient quantities.

For many samples of current interest in the semiconductor circuit fabrication industry it is not practical to measure the change $\Delta T$ in the transmission of the probe light pulse. The films are normally deposited onto silicon substrates of thickness around 0.02 cm. Unless light of wavelength of one micron or greater is used, the light will be heavily absorbed in the substrate making the measurement of the transmission very difficult. For such samples conventional methods are thus essentially limited to the use of the measurement of the change $\Delta R$ in the optical reflectivity induced by the pump pulse. Many samples of interest include a series of films deposited sequentially onto the substrate. This type of structure can be referred to as a "stack". When stress pulses are generated in a stack a very complicated response (for example, the result of a measurement of $\Delta R(t)$) may be obtained. This complex response results from the generation of stress pulses in various different parts of the structure, the propagation of these pulses with partial transmission and partial reflection across the interfaces into other films, and the change in the intensity reflection coefficient of the structure due to the strain-induced change in the optical properties of each film. To determine the thickness of a number of the films in a stack requires the determination of the times at which stress pulses originating at known places in the structure are reflected or transmitted at the various interfaces. From these times, and using assumed velocities for the different films, the thicknesses of the films can be found. The determination of the times just referred to requires the identification of the different features that appear in the response $\Delta R(t)$. With the arrangement available in conventional systems the identification of the origin of the various features may be extremely difficult and/or time-consuming for a multi-layer structure. It is often necessary to make a guess that a particular feature arises from a stress pulse which originates at a particular location and has undergone a certain sequence of transmissions and reflections at different interfaces. In addition, it may be the case that a certain feature of interest, such as the arrival of a stress pulse at one particular interface, gives a response which happens to be dominated or masked by a larger response from another stress pulse reaching a different part of the structure at approximately the same time. The present invention overcomes these difficulties as follows.

As mentioned above, in the prior art the primary measured quantity for most samples of current technical interest is the change $\Delta R(t)$ in optical reflectivity. If the response $\Delta R(t)$ is difficult to analyze, then it is also difficult to deduce the required information about the structure, for example the thicknesses of the different films. This difficulty may be overcome by measurements of $\Delta P$, $\Delta \phi$, or $\Delta \delta$. For example, a particularly important feature may appear as a very small response in $\Delta R(t)$, but may make a dominant response in $\Delta P(t)$, $\Delta \phi(t)$, or $\Delta \delta(t)$.

In accordance with an aspect of this invention the non-destructive system and method is enabled to also simultaneously measure at least two transient responses of the structure to the pump pulse. The simultaneously measured transient responses comprise at least two of a measurement of the modulated change $\Delta R$ in an intensity of a reflected portion of a probe pulse, the change $\Delta T$ in an intensity of a transmitted portion of the probe pulse, the change $\Delta P$ in the polarization of the reflected probe pulse, the change $\Delta \phi$ in optical phase of the reflected probe pulse, and the change in an angle of reflection $\Delta\delta$ of the probe pulse. The measured transient responses are then associated with at least one characteristic of interest of the structure.

However, even when the measurement of $\Delta P(t)$, $\Delta\phi(t)$, or $\Delta\delta(t)$ does not show a response in which the feature of primary interest dominates, it may still be possible to effectively isolate the response of interest by a "differential method" (DM). That is, by taking a suitable linear combination of the different measured responses it may be possible to enhance the magnitude of the response of interest and reduce the size of the other competing response or responses.

The same type of DM procedure as just described can also be accomplished by making simultaneous or sequential measurements of one or more of the quantities $\Delta R(t)$, etc. at more than one wavelength of the pump and/or the probe, or angle of incidence of the pump and/or the probe, or polarization of the pump and/or the probe beams.

The same type of DM procedure can also be achieved for some samples by making measurements at more than one intensity of the pump and/or probe beams. The point is that the responses, such as the change in reflectivity $\Delta R(t)$, for example, may vary non-linearly with the intensity and/or the duration of the pump and/or probe pulses. Thus, again by taking suitable linear combinations of the responses measured at different intensities or pulse durations, it may be possible to enhance a portion of the response arising from one effect at the expense of competing effects.

The picosecond ultrasonic system in accordance with the teaching of this invention can also employ the simultaneous or sequential measurement of the ellipsometric parameters of the sample using signals corresponding to one or more suitable non-pulsed additional light sources (e.g., the He—Ne laser 136) whose optical path may or may not have some or all optical components in common with the means for directing the pulsed laser beams to and from the sample. This overcomes some of the difficulties of conventional systems in a manner similar to the methods described above.

An automatic adjustment of the position and orientation of the sample to achieve a desired overlap of the pump and probe beams on the sample surface can also be employed, in conjunction with the control of the spot size on the sample of one or both of the pump and probe lasers. This is accomplished, as described in reference to FIGS. 16–20, with a means for detecting one or both beams after they impinge on the sample, and a means for adjusting the height and tilt of the sample with respect to the beams to achieve the desired focusing conditions. This approach is superior to the manual adjustment techniques taught by the prior art, in that an automatic adjustment scheme overcomes the difficulty of a slow and unreliable manual adjustment which is incompatible with the need to make rapid and accurate measurements in an industrial environment. Furthermore, the reproduce ability of measurements between samples is also improved.

It is also within the scope of this invention to provide a picosecond ultrasonics system using one or more modulators of the pump or probe beams in which the modulation drive signal for one or more of the modulators, and the pulse rate of one or more pulsed lasers, are derived from a common clock. In addition, it is also within the scope of the teaching of this invention that the modulation of the pump or probe beam is derived from the pulse rate of one or more of the pulsed lasers in the system. This overcomes a problem in the prior art, wherein the modulation is not synchronized with the repetition rate of the laser or lasers. Thus, in each modulation cycle there can be a variation in the number of probe or pump pulses contained in one modulation cycle according to the instantaneous phase of the modulator relative to the timing of the laser pulses. This variation contributes to the noise of the system, and is advantageously eliminated in the present invention.

This invention further teaches a picosecond ultrasonic system in which measurements for a particular sample are made at at least two temperatures for the purpose of detecting the change in the sound velocity in one or more layers in response to the temperature change. The temperature change may be induced by a heat lamp directed at the surface of the sample, by a resistive heater in contact with the rear of the sample, by the average heating of the sample by the pump light pulses, or by the use of another light source directed through some of the same optical elements used to guide the pump and/or probe beams onto the sample (or via some other optical system). The stress in one or more layers is determined by relating the observed change in the sound velocity in one or more layers determined at two or more temperatures to the stress in the layer or layers.

As has been described, it has been established experimentally that the temperature-dependence of the sound velocity depends on the static stress. This provides the basis for this aspect of the invention.

It is important to note that the application of this method does not require a measurement of the absolute value of the sound velocity, but only the change of the velocity with temperature. This is an important point, since to determine the absolute velocity it would be necessary to have a very precise value for the film thickness. To determine the temperature-dependence of the sound velocity, on the other hand, requires only a measurement of the temperature-dependence of the acoustic transit time. To determine the temperature-dependence of the sound velocity from this quantity it is necessary only to apply a correction to allow for the thermal expansion of the sample.

This invention further teaches a picosecond ultrasonic system which directly measures the derivative with respect to time delay between the pump and probe beams of some or all of the quantities listed above, i.e., (1) the small modulated change $\Delta R$ in the intensity of the reflected probe beam, (2) the change $\Delta T$ in the intensity of the transmitted probe beam, (3) the change $\Delta P$ in the polarization of the reflected probe beam, (4) the change $\Delta\phi$ in the optical phase of the reflected probe beam, and/or (5) the change in the angle of reflection $\Delta\delta$ of the probe beam. To achieve the measurement of the derivative the probe pulse delay is varied periodically over a small range by means of an oscillating optical component in the pump or probe path. A frequency range of 10 Hz to 1 MHz is suitable for this purpose.

One advantage of this method is as follows. In many applications one is interested in the time of arrival of acoustic echoes at certain points in the sample. These acoustic echoes appear as sharp features in the measured reflectivity change $\Delta R(t)$ as a function of time. These echoes can be enhanced relative to the background if the system directly measures the derivative of $\Delta R$ (or the other quantities listed above) with respect to time, rather than $\Delta R$ itself.

This invention further teaches a picosecond ultrasonic system which incorporates an optical fiber or fibers for any of the following purposes: (a) guiding the laser beam between different parts of the optical system; (b) guiding the pump and/or probe to the sample; (c) collecting the reflected or transmitted probe from the sample; and/or (d) maintaining a constant probe output profile and position for varying input conditions.

The picosecond ultrasonic system in accordance with this invention may incorporate light sources with any of the following features.

A first feature employs a pulsed laser with the output directed to an optical harmonic generator or generators, as in FIGS. 19 and 20. The outputs of the harmonic generator 138 and/or the unmodified output of the laser are thus used for the pump and/or probe beams. This improves on conventional practice in that it allows for the rejection of the pump light at the detector of the probe beam so as to improve the signal to noise ratio. Also, for certain samples the most advantageous wavelength for the generating pump beam may be different from the optimum wavelength for the probe beam.

A second feature employs one or more of the polarizing beam splitters which are used to continuously vary the ratio of the pump and probe beams under computer control. The ratio can be controlled to optimize the signal to noise for a given sample. It may be advantageous to change the ratio to achieve the best performance for samples with particular characteristics.

This invention further teaches a picosecond ultrasonic system that incorporates different repetition rate lasers to effect a delay as an alternative approach to a mechanical delay stage. This has the advantage that a mechanical stage is not required. In addition, the data can be acquired very quickly, provided that the signal-to-noise ratio is acceptable.

This invention further teaches a picosecond ultrasonic system that employs a multi-element delay stage. This has the advantage that the delay of the probe pulse is increased for a given distance moved by the mechanical stage. Thus, the distance travelled by the stage in order to produce a given delay of the probe pulse can be decreased.

Furthermore, the invention teaches the measurement of the transient optical properties of the sample using a probe pulse that is derived from an output pulse of the laser that is different from the output pulse used for the pump. This enables the production of a large effective delay for the probe, without requiring that a very long optical path difference be established in the system.

The invention also teaches a picosecond ultrasonic system which may include suitable additional optical sources, including additional lasers as well as white light sources. These sources may be directed to the sample by a guiding system which may include some elements in common with the pulsed pump and probe beam paths. These additional light sources may be used to effect ellipsometry or reflectometry, or to illuminate the sample for inspection purposes, or to raise the temperature at a particular location.

In one aspect the invention provides a picosecond ultrasonic system that incorporates the color filter F1 in the path of the probe beam after it has been reflected or transmitted at the sample for the purpose of suppressing scattered pump light. This embodiment is employed to advantage when the pump and probe sources have different wavelengths. The suppression of the pump light improves the signal to noise ratio when the sample surface is non-specular, and where the incident pump light is scattered at the sample surface.

The invention further provides a picosecond ultrasonic system that incorporates optical elements for delivering the probe beam to the sample, and which allows the location, shape and/or size of the probe spot on the sample to be kept substantially constant and free from changes due or the variation of the optical path length of the probe. This is a more general case than the above-mentioned use of an optical fiber for a similar purpose. Furthermore, "active" correction schemes can be employed in which the characteristics of the probe spot are sensed, and in which the characteristics of probe beam (e.g., profile and (location) are adaptively corrected.

The invention further teaches a picosecond ultrasonic system that incorporates an optical guiding system in which the pump and probe beams are focused separately onto the sample. The pump and probe beams may be scanned laterally relative to each other. In particular, a guiding and focusing system can be employed in which the probe beam is guided through an optical fiber assembly with a tapered end which effects near field focusing into a spot which is smaller than the pump beam, and which may be scanned over small displacements relative while the pump beam is held substantially stationary. The use of a reduced tip fiber makes it possible to achieve spots for the pump and probe with dimensions as small as 1000 Å.

It is thus possible to investigate the properties of a sample through the study of waves propagating across the surface from one point to another. A second purpose is to generate bulk waves which travel through the sample from the pumped region to the probe spot. Other applications pertain to structures that are laterally patterned. In this case the pump light may be directed so as to be absorbed in a "dot", i.e. a film which has a very small area. Stress waves generated in this dot then propagate to the region of the structure that is sensed by the probe pulse.

Also disclosed is a picosecond ultrasonic system in which the results of measurements are compared with computer simulations of the measured response or responses (1)–(5), for example. To perform the simulation the following steps are performed. Reference is also made to the flow chart of FIG. 21.

(A) Initial Stress Distribution

The stress distribution in the sample produced as a result of the absorption of the pump pulse is calculated using known values for the optical absorption of the various materials present in the sample, the specific heats of these materials, the thermal expansion coefficients, and the elastic constants. To calculate the stress distribution the effect of thermal diffusion may be taken into account. For a sample composed of several planar films of different materials with material properties uniform throughout each film the following procedure is used.

From the optical constants and thicknesses of the films the electric field due to the pump light pulse at all points in the structure is calculated in terms of the amplitude, angle of incidence, and polarization of the pump beam incident on the sample surface. This calculation is most readily performed through the use of optical transfer matrices. Next, from the calculated electric field distribution, the energy absorbed in the structure as a function of position is calculated. Next, the effect of thermal diffusion on the absorbed energy distribution is considered. Next, the temperature rise of each part of the sample is calculated. This temperature rise is the energy deposited per unit volume divided by the specific heat per unit volume. Next, the stress at all points in the sample is then calculated from the temperature rise by multiplying the temperature rise by the thermal expansion coefficient and the appropriate elastic modulus.

Change in Stress and Strain with Time

The change in stress and strain in the sample is next calculated as a function of time and position using the laws of physical acoustics. This calculation is effectively performed by means of a "stepping algorithm", which performs the following computations.

First, a time step $\tau$ is chosen. For each film or layer that comprises the structure of interest a bin size b equal to the time τ multiplied by the sound velocity in the film is then calculated. Each film is then divided into bins of this size or smaller. By example, smaller size bins can be employed at any film boundary. The time step τ is chosen so that each film preferably contains a large number of bins. The results of the foregoing give the stress set up by the pump pulse in each bin of the structure. Next, the stress in each bin is decomposed into two components, one initially propagating towards the free surface of the sample and one away from it. Within a given film these two components are stepped forward from bin to bin in the appropriate direction. For a bin adjacent to the boundary between two films the stress propagating towards the boundary is stepped partly into the first bin on the other side of the boundary and still propagating in the same direction and partly into the original bin but propagating in the reverse direction. The fraction of the stress that is stepped across the interface and the fraction which reverses direction are calculated from the laws of physical acoustics. At the top (free) surface of the structure the stress in the bin adjacent to the surface and propagating towards the surface remains in the same bin but has its direction reversed, i.e., it becomes a stress pulse propagating into the interior of the structure rather than towards the top surface. By applying this procedure to all bins for a sufficient number of time steps τ, the stress distribution can be calculated for as long a time as is required for comparison with the measured results. From the calculated stress the strain is calculated by division by the appropriate elastic coefficient.

Samples that are of interest in chip fabrication typically have a number of thin films deposited on top of a semiconductor substrate. Presently, the total thickness of these thin films is a few microns or less, whereas the substrate is typically approximately 200 microns thick. An important advantage of this "stepping method" is that it is not necessary to consider stress propagation throughout the entire substrate. Instead it is normally sufficient to consider just one bin of the substrate together with "boundary conditions" specified as follows.

(1) At each time step r the stress within the single bin of the substrate and propagating towards the substrate can be considered to be completely transferred into the remainder of the substrate so that no part of this stress is reflected. (2) The stress within the substrate bin and propagating towards the film structure is taken to be zero. This description of the treatment of the substrate holds if the amount of light that reaches the substrate, after passing through whatever films are deposited onto the substrate, is negligible. This condition holds for the majority of structures which are of current industrial interest.

When this condition is not satisfied, and light does reach the substrate, it is desirable to include in the simulation a thickness of the substrate sufficient to include the entire depth over which the pump or the probe light can significantly penetrate. This depth is typically some number, e.g. five, of absorption lengths of the pump or probe light. This region of the substrate is then divided into bins of thickness as specified above. The last bin of the substrate is then treated according to the following boundary conditions.

First, at each time step the stress within the last bin of the substrate, and propagating towards the interior of the substrate, can be considered to be completely transferred into the remainder of the substrate so that no part of this stress is reflected. Second, the stress within the last bin of the substrate, and propagating towards the film structure, is taken to be zero.

For some samples the above division of the simulation into the consideration of the calculation of the temperature rise and the propagation of the stress may not be applicable. It is noted that, as soon as energy is deposited into any part of the sample, a stress is set up and mechanical waves are launched into adjacent regions. If the diffusion of energy is sufficiently large and continues for a sufficient period of time then the changing temperature and associated stress distribution in the sample will continue to generate new stress waves. However, the extension of the simulation to include this effect is straightforward.

In some samples, particularly metal films of high electrical conductivity, a more detailed treatment of the diffusion of energy is required. The energy in the pump light pulse is initially input to the conduction electrons, thereby raising their energy considerably above the Fermi level. These electrons have a very high diffusion coefficient and may spread a significant distance through the sample before losing their excess energy as heat to the lattice. Under these conditions the diffusion of the energy is not adequately described by Fourier's law for classical heat conduction. Instead it is preferred to use a more microscopic approach, taking into account the diffusion rate of the electrons and the rate at which they lose energy.

(C) Calculation of the Transient Response Measured by the Probe

From the calculated strain distribution as a function of depth into the sample, the changes $\Delta n$ and $\Delta \kappa$ in the optical constants are calculated. This step requires knowledge of the derivatives of the optical constants $\eta$ and $\kappa$ with respect to elastic strain.

From the calculated changes $\Delta \eta$ and $\Delta \kappa$ in the optical constants as a function of depth, and the unperturbed optical constants of the films, at least one of the quantities $\Delta R$, $\Delta T$, $\Delta P$, $\Delta \phi$ and $\Delta \beta$ is calculated and compared with the measured results. This calculation is most conveniently carried out through the use of optical transfer matrices.

The above description of the simulation steps A–C is presented in terms of a one-dimensional model considering only the variation of the electric field of the probe light, the elastic stress, the elastic strain, etc., upon the distance along the direction normal to the surface of the sample. It is within the scope of this invention to extend the calculations to allow for the variation in the intensity of the pump and probe beams within the plane of the surface of the sample. This approach is useful for the calculation of the change in the propagation angle of the reflected probe light $\Delta \delta$.

A series of such simulations are performed in which the assumed thicknesses of the films in the structure are varied. By comparison of the results of the simulation with some or all of the measured quantities $\Delta R$, $\Delta T$, $\Delta P$, $\Delta \phi$ and $\Delta \delta$ the thicknesses of the films are determined.

It is also within the scope of this invention to adjust the film thicknesses so as to be consistent with results of any or all of: (a) measurements of the optical reflectivity through measurements of the incident and reflected average intensity of the pump and/or probe beams; (b) measurements of the average phase change of the pump and/or probe beams upon reflection; and (c) measurements of the average polarization and optical phase of the incident and reflected pump and/or probe beams.

It is further within the scope of the teaching of this invention to include simulations which incorporate as adjustable parameters at least one of the following for one or more films in order to find a best-fit to measured data.

A first adjustable parameter is the film thickness, so as to adjust the thicknesses obtained in accordance with the method described above.

In this regard reference can be had to an article entitled "Time-resolved study of vibrations of α-Ge:H/α-Si:

multilayers", Physical Review B, vol. 38, no. 9, Sep. 15, 1988, H. T. Grahn et al., wherein reference is made to a simulation of a multilayer structure and a variation in layer thickness (as well as sound velocities). As was reported in this article, it was not possible to find parameters such that the simulated response was in agreement with an experimentally observed $\Delta R(t)$. Reference may also be had, by example, to the following articles that were also coauthored by one of the inventors of this patent application: "Sound velocity and index of refraction of AlAs measured by picosecond ultrasonics", Appl. Phys. Lett. 53 (21), Nov. 21, 1988, pp. 2023–2024, H. T. Grahn et al.; "Elastic properties of silicon oxynitride films determined by picosecond acoustics", Appl. Phys. Lett. 53 (23), Dec. 5, 1988, pp. 2281–2283, H. T. Grahn et al.; and "Study of vibrational modes of gold nanostructures by picosecond ultrasonics", Appl. Phys. 73 (1), Jan. 1, 1993, pp. 37–45, H. N. Lin et al.

A second adjustable parameter is the sound velocity. An example of a situation in which one may determine the sound velocity has been described above. Thus, in this context what is taught is the determination of the parameters n, d, and v by comparison of the measured data with simulations, rather than by a measurement of the frequency $f(\theta)$ as a function of the angle $\theta$.

A third adjustable parameter is the crystal orientation in a film. This can be achieved through measurement of the sound velocity, which is dependent on crystal orientation in all crystals, even those with cubic symmetry. In non-cubic crystals the crystal orientation of the film, or the preferential orientation of crystalline grains, leads to anisotropic optical properties which can be detected via the measurements of the above described optical measures of the optical reflectivity by determining the incident and reflected average intensity of the pump and/or probe beams; the average phase change of the pump and/or probe beams upon reflection; and/or the average polarization and optical phase of the incident and reflected pump and/or probe beams.

A fourth adjustable parameter is interface roughness. By example, the interface roughness parameter causes a broadening of a stress pulse which is transmitted across, or reflected at, the interface.

A fifth adjustable parameter is the interface adhesion strength, as will be described in further detail below.

A sixth adjustable parameter is the static stress. One suitable procedure by which this can be determined has been described previously in the context of measurements made at two or more temperatures of the sample.

A seventh adjustable parameter is the thermal diffusivity. The thermal diffusivity of the different films in the sample affects the shape and magnitude of the generated stress pulses. By treating the thermal diffusivity as an adjustable parameter, and selecting it to give the best agreement between the simulation and the measured data, the thermal diffusivity of a particular film in the structure can be determined.

An eighth adjustable parameter is the electronic diffusivity. In some samples which contain metal films with high electrical conductivity the diffusion of the conduction electrons before they lose the energy that they have received from the pump pulse has a large effect on the shape and magnitude of the stress pulses which are generated. By treating the electronic diffusivity as an adjustable parameter, and adjusting it to give the best agreement between the simulation and the measured data, the electronic diffusivity of a particular film in the structure can be determined.

It should be appreciated that the seventh and eight adjustable parameters provide, separately or in conjunction with one another, a means for the determination of the electrical resistance of metallic films.

A ninth adjustable parameter involves the optical constants of the film(s) and/or substrate.

A tenth, related adjustable parameter is the derivatives of the optical constants with respect to stress or strain.

An eleventh adjustable parameter is the surface roughness. The surface roughness has the consequence that a stress pulse reflected at the surface of a sample is broadened. This broadening may be introduced into the simulation and adjusted until the simulation gives the best agreement with the measured data. In this way the surface roughness can be determined.

A twelfth adjustable parameter is interfacial contamination. If an interface between two materials A and B is contaminated by the presence of a thin layer of another material C, the presence of the layer C affects the reflection and transmission coefficients for stress waves incident on the interface. For two elastic media in perfect mechanical contact the reflection and transmission coefficients are given by well-known formulas from physical acoustics. The effect of interface adhesion strength on the coefficients is discussed below. The coefficients may also be affected by other effects which are unrelated to adhesion strength. For example, in addition to changing the strength of the coupling between A and B (i.e., the adhesion strength) the contamination layer C provides a layer of mass at the interface which affects the acoustic propagation. The contamination layer C may also lead to additional optical absorption at the interface. The additional optical absorption of the pump pulse will in this case result in additional stress waves to be generated at the interface. The detection of these additional stress waves provides a means for detecting the presence of the contamination layer C. This method can be applied to advantage for detecting contamination on the surface of optically transparent bulk materials.

A thirteenth adjustable parameter is related to dimensions other than thickness and geometrical shape. These parameters are generally not relevant to measurements on samples consisting solely of planar films. Instead, these adjustable parameters enter into the characterization of samples of the type mentioned above with respect to laterally patterned structures and the like. These adjustable parameters apply as well to the characterization of an array of identical structures having dimensions much less than the pump and probe spot diameter, as described below.

A further adjustable parameter relates to the presence of and thickness of a region of intermixing between two adjacent layers.

An important aspect of this invention concerns the precise relation between the computer simulations and the transient optical responses measured by the system. The following discussion describes the essential aspects of this relation for the particular example of a sample containing a number of planar films whose lateral extent is much greater than their thickness, and also greater than the linear dimensions of the region of the sample illuminated by the pump and probe pulses. A generalization of this discussion to laterally patterned structures will be evident to workers skilled in the relevant art, when guided by the following teachings. Similarly, the following discussion will consider, again as a specific example, a particular one of the transient optical responses, namely the change $\Delta R(t)$ in optical reflectivity. The generalization of the discussion to a consideration of the other transient optical responses aforementioned should also become evident to workers skilled in the relevant art, when guided by the following teachings.

In this example the computer simulations calculate the change in the optical reflectivity $\Delta R_{sim}(t)$ of the sample when it is illuminated with a pump pulse of unit energy per unit area of the sample. The simulation also gives a value for the static reflection coefficient of the pump and probe beams. The system measures the transient change $\Delta P_{pro-refl}$ in the power of the reflected probe pulse as determined, for example, by photodiode D1 in FIG. 18. It also measures the static reflection coefficients of the pump and probe beams from a ratio of the power in the incident and reflected beams. The incident probe power is measured by photodiode D2 in FIG. 18, the reflected probe power is measured by D1, the incident pump power is measured by D4, and the reflected pump power is measured by D3.

To relate the simulation results for the transient change in the optical reflectivity to the system measurement it is necessary to know: (a) the power of the pump and probe beams; (b) the intensity profiles of these beams; and (c) their overlap on the sample surface.

Let us suppose first that the pump beam is incident over an area $A_{pump}$ and that within this area the pump intensity is uniform. Then for each applied pump pulse the pump energy absorbed per unit area is $$\frac{P_{pump-inc}}{A_{pump}} \frac{(1 - R_{pump})}{f} \quad (3)$$

where f is the repetition rate of the pump pulse train, and $R_{pump}$ is the reflection coefficient for the pump beam. Thus, the change in optical reflectivity of the each probe light pulse will be $$\Delta R_{sim}(t) \frac{P_{pump-inc}}{A_{pump}} \frac{(1 - R_{pump})}{f} \quad (4)$$

and the change in power of the reflected probe beam will be $$\Delta P_{probe-refl} = P_{probe-inc} \Delta R_{sim}(t) \frac{P_{pump-inc}}{A_{pump}} \frac{(1 - R_{pump})}{f} \quad (5)$$

In a practical system the illumination of the sample does not, in fact, produce a uniform intensity of the incident pump beam. Moreover, the intensity of the probe light will also vary with position on the sample surface. To account for these variations the equation for $\Delta P_{probe-refl}$ is modified to read $$\Delta P_{probe-refl} = P_{probe-inc} \Delta R_{sim}(t) \frac{P_{pump-inc}}{A_{effective}} \frac{(1 - R_{pump})}{f} \quad (6)$$

where the effective area $A_{effective}$ is defined by the relation where $I_{probe-inc}(\vec{r})$ and $I_{pump-inc}(\vec{r})$ are respectively the $$A_{effective} = \frac{\int I_{pump-inc}(\vec{r}) dA \int I_{probe-inc}(\vec{r}) dA}{\int I_{pump-inc}(\vec{r}) I_{probe-inc}(\vec{r}) (dA}  \quad (7)$$

intensities of the probe and pump beams on the surface of the sample. One can consider $A_{effective}$ to be an effective area of overlap of the pump and probe beams.

Analogous expressions can be derived for the change in optical transmission $\Delta T(t)$, the change in optical phase $\Delta \phi(t)$, the change in polarization $\Delta P(t)$, and the change $\Delta \beta(t)$ in the angle of reflection of the probe light.

The following quantities are measured by the system: $\Delta P_{probe-refl}, P_{probe-inc}, P_{probe-inc}, R_{pump}, R_{probe}$. The computer simulation gives predicted values for $\Delta R_{sim}(t)$, $R_{pump}$ and $R_{probe}$. Thus the following comparisons can be made between the simulation and the system measurements in order to determine the characteristics of the sample.

(1) A comparison of the simulated and measured reflection coefficient $R_{pump}$.

(2) A comparison of the simulated and measured reflection coefficient $R_{probe}$.

(3) A comparison of the simulated and measured transient change $\Delta P_{probe-refl}$ in the power of the reflected probe light.

To make a comparison of the simulated and measured change, it can be seen from the preceding equation (6) that it is necessary to know the value of $A_{effective}$. This can be accomplished by one or more of the following methods.

(a) A first method directly measures the intensity variations of the pump and probe beams over the surface of the sample, i.e, $I_{probe-inc}(\vec{r})$ and $I_{pump-inc}(\vec{r})$ as a function of position, and uses the results of these measurements to calculate $A_{effective}$. This is possible to accomplish but requires very careful measurements which may be difficult to accomplish in industrial environment.

(b) A second method measures the transient response $\Delta P_{probe-refl}$ for a sample on a system S for which the area $A_{effective}$ is known. This method then measures the response $\Delta P_{probe-refl}$ of the same sample on the system S' for which $A_{effective}$ is to be determined. The ratio of the responses on the two systems gives the inverse of the ratio of the effective areas for the two systems. This can be an effective method because the system S can be chosen to be a specially constructed system in which the areas illuminated by the pump and probe beams are larger than would be desirable for an instrument with rapid measurement capability. Since the areas are large for this system it is simpler to measure the intensity variations of the pump and probe beams over the surface of the sample, i.e, $I_{probe-inc}(\vec{r})$ and $I_{pump-inc}(\vec{r})$ as a function of position. This method is effective even if the quantities which enter into the calculation of the simulated reflectivity change $\Delta R_{sim}(t)$ are not known.

(c) A third method measures the transient response $\Delta P_{probe-refl}$ for a sample in which all of the quantities are known which enter into the calculation of the simulated reflectivity change $\Delta R_{sim}(t)$ of the sample when it is illuminated with a pump pulse of unit energy per unit area of the sample. Then by comparison of the measured transient response $\Delta P_{probe-refl}$ with the response predicted from the Eq. 6 the effective area $A_{effective}$ is determined.

To build a truly effective instrument it is essential that the effective area $A_{effective}$ be stable throughout the course of a sequence of measurements. To ensure this, the system of this invention incorporates means for automatically focusing the pump and probe beams onto the surface of the sample so as to achieve a reproducible intensity variation of the two beams during every measurement. The automatic focusing system provides a mechanism for maintaining the system in a previously determined state in which the size and relative positions of the beams on the sample surface are appropriate for effective transient response measurements.

It should be noted that for any application in which the amplitude of an optical transient response is used to draw quantitative conclusions about a sample (for example, when the magnitude of a feature that arises from an acoustic echo is influenced by the condition of a buried interface) a calibration scheme such as described above must be a feature of the measurement system.

The preceding description of the method for the comparison of the computer simulation results and the system measurements supposes that the several detectors in the measurement system are calibrated. It is contemplated that such a system will use detectors operating in the linear range so that the output voltage V of each detector is proportional to the incident optical power P. For each detector there is thus a constant G such that V=GP. The preceding description assumes that the constant G is known for each and every detector. In the case that this information is not available, the individual calibration factors associated with each of the individual detectors measuring $P_{probe-inc}$, $P_{pump-inc}$, and $\Delta P_{probe-refl}$ may be combined with $A_{effective}$ and f into a single overall system calibration constant C. Therefore in terms of a calibration factor C, Eq. 6 could be expressed as $$\Delta V_{probe-refl} = C\, V_{probe-inc} \Delta R_{sim}(t)\, V_{pump-inc}(1-R_{pump}) \quad (8)$$

where $\Delta V_{probe-refl}$ is the output voltage from detector used to measure the change in the power of the reflected probe light (D1), $V_{pump-inc}$ is the output voltage from the detector used to measure the incident pump light (D4), and $V_{probe-inc}$ is the output voltage of the detector used to measure the incident probe light (D2). Thus, to provide an effective instrument it is sufficient to determine the constant C. This can be accomplished by either of the following two methods.

(a) A first method measures the transient response $\Delta V_{probe-inc}$ for a sample in which all of the quantities are known which enter into the calculation of the simulated reflectivity change $\Delta R_{sim}(t)$ of the sample when it is illuminated with a pump pulse of unit energy per unit area of the sample. Next, the method measures $V_{probe-inc}$ and $V_{pump-inc}$, then determines $R_{pump}$ either by measurement or from the computer simulation. The method then finds the value of the constant C such that Eq. 8 is satisfied.

(b) A second method measures the transient response $\Delta V_{probe-refl}$ for a reference sample for which the transient optical response $\Delta R(t)$, when it is illuminated with a pump pulse of unit energy per unit area of the sample, has been measured using a system which has been previously calibrated, for example, by one or more of the methods described above. The method then measure $V_{probe-inc}$ and $V_{pump-inc}$, determines $R_{pump}$ by measurement, and then finds the value of the constant C such that the following equation is satisfied.

$$\Delta V_{probe-refl} = C\, V_{probe-inc} \Delta R(t)\, V_{pump-inc}(1-R_{pump}) \quad (9)$$

For both of these methods it is important to establish the autofocus conditions prior to making measurements of $\Delta V_{probe-refl}$, since C depends on the value of $A_{effective}$.

The teaching of this invention furthermore encompasses a picosecond ultrasonic system in which the results of measurements are compared with computer simulations of the measured response, as described above, but using a different method to perform the simulation. In this case the following steps may be employed.

First, the initial stress distribution in the structure is calculated using the method described above.

Second, the acoustical normal modes of the structure are calculated through solution of the equations of physical acoustics together with appropriate boundary conditions at the interfaces between the films, at the free surface of the sample, and at the free surface of the substrate. All normal modes up to certain maximum frequency $f_{max}$ are calculated. The choice of this maximum frequency is related to the sharpness of the features, such as echoes, that appear in the measured data. As an approximate rule, if it is desired to simulate data for a structure of interest which has a characteristic time-scale $\tau$, it is necessary to choose $f_{max}$ such that the product of $f_{max}$ and $\tau$ is at least as large as unity. Thus, for example, if the measured data contains an echo of width 1 psec, then to perform an accurate simulation it is desirable to calculate all normal modes up to the frequency 1000 GHz.

The substrate thickness is typically in the range around 200 microns, whereas often the total thickness of the thin films deposited onto the substrate is a micron or even less. A calculation of the normal modes of a sample consisting of films on a substrate of this thickness is very difficult and time-consuming because of the very large number of acoustic modes with very closely-spaced frequencies. However, for the purposes of creating an accurate simulation of the typical data on this type of sample it is not necessary to use the actual thickness of the substrate. Instead it is sufficient to consider the "substrate" to have a thickness much less than the real physical substrate. The thickness of this artificial substrate should be sufficiently large such that the time required for an acoustic wave to propagate through the substrate from the thin films deposited on the front surface of the substrate to the far side of the substrate and back again is longer than the total time span over which the data to be simulated extends. Thus, for example, if the data extends from zero time delay of the probe relative to the pump to a time delay of 1000 psecs, and the sound velocity v in the substrate is $5 \times 10^5$ cm sec$^{-1}$, then the artificial substrate can be taken to have a thickness of as little as 2.5 microns. If the thickness is at least this great no acoustic echoes can return from the back of the substrate during the time that measurements are made, and hence the difference in thickness between the artificial substrate and the actual substrate is irrelevant.

Third, the initial stress distribution produced by the pump beam is decomposed into a sum over the normal modes just calculated. It is possible to choose a set of amplitudes for the normal modes such that when the contributions of each normal mode are added together, taking allowance for the amplitude of each mode, the initial stress distribution is accurately reproduced. The initial amplitude of the nth normal mode may be denoted as $A_n$.

Fourth, each normal mode has a characteristic spatial stress pattern associated with it. This stress pattern gives a change in the reflection coefficient of the probe light which can be calculated according to the methods described above. Let this change when the nth mode has unit amplitude be $B_n$. This change is linear in the amplitude of the acoustic normal mode. Hence, the total change in the reflectivity of the probe light at time zero is $$\Delta R(t=0) = \text{sum}_n A_n B_n. \quad (10)$$

Fifth, let the frequency of the nth normal mode be $f_n$. Then the total change in reflectivity of the probe light at any later time t can be calculated as $$\Delta R(t) = \text{sum}_n A_n B_n \cos(2\pi f_n t). \quad (11)$$

This simulation method has the advantage that through the use of the formula just given the change in reflectivity at any chosen time, or within any chosen time range, may be calculated without the need to consider the acoustic or optical processes occurring in the sample for all times intermediate between the application of the pump pulse and the time of interest. It is important to note that the amplitudes $A_n$ and the coefficients $B_n$ need be calculated only once, and can then be used to find the response at any later time.

It should be further noted that the above description refers to the use of this method for the calculation of the change in reflected intensity of the probe beam. However, completely analogous methods can be used to simulate the other responses of interest, i.e. $\Delta T$, $\Delta P$, $\Delta\phi$, and $\Delta\delta$.

As was indicated previously, the teaching of this invention is also directed to a picosecond ultrasonic system which enables the measurement of a vibrational response of a sample that includes, by example, a very thin film on a substrate, or a very thin film on a significantly thicker film. By example, a substrate may have a layer of a metal, such as aluminum, and an intervening layer comprised of a polymer. The measured response is then analyzed to determine the damping rate of the thickness vibration of the film. This damping rate is compared with a damping rate determined for a model based on classical acoustics in which the interface between the thin film and the substrate (or thicker film) is characterized by a coupling parameter ("adhesion strength") per unit area. This coupling parameter, which may be considered to be a spring constant parameter that is a linear property per unit area, is the strength, of a spring per unit area which connects the surface of the thin film to the substrate, or to the thicker film. The adhesion strength is adjusted to give agreement between the simulation and the measured value of the damping, and is thus used as a measure of the quality of the interface.

As was also indicated previously, the teaching of this invention furthermore pertains to a picosecond ultrasonic system in which a sample is comprised of an array of identical structures having dimensions much less than the pump and probe spot diameter. In this case each structure is simultaneously excited by the pump beam and then simultaneously examined by the probe beam. The response of each structure is simulated by the methods described above. The characteristics of the structures are then deduced by comparison of the simulation and the measured response.

Relatedly, this invention also teaches methods for deducing the dimensions of substantially identical patterned structures arranged periodically, and for deducing the statistical distribution of sizes of such structures. This is accomplished by comparing the observed response of the structures, to a stress pulse that is induced by the pump pulse, to simulations of the array of vibrating structures.

Further in this regard, the teaching of this invention also pertains to methods for deducing the physical characteristics of thin films patterned mechanically or by lithographic means into structures. Steps of the method include simulation of the mechanical vibrations of a single structure, calculation of the change in the probe beam after it impinges on the structure, and adjusting the physical characteristics of the simulated structure and interfaces in order to obtain a best fit to the observed response.

Further in accordance with the teaching of this invention, a picosecond ultrasonic system employs a method for deducing the physical characteristics of a sample, and uses an analysis of an acoustic echo or echoes based on either or both of the following two methods.

In a first method a characterization of the time of arrival of an echo is obtained by means of the location in time of one or more echo features, such as a point of maximum or minimum amplitude or inflection point.

In a second method a characterization of the time of arrival of the echo as seen in $\Delta R(t)$ (or, by example, $\Delta T(t)$, $\Delta P(t)$, $\Delta\phi(t)$, and $\Delta\delta(t)$) by convolution of the measured echo with a suitably chosen function f(t) of the time. Thus, the convolution $$C(t_1) = \int \Delta R(t)\, f(t-t_1)\, dt \qquad (12)$$

is calculated. The time $t_1$ is then adjusted so as to maximize the result of the convolution, i.e. to maximize C. The resulting value of $t_1$ is then used as an estimate of the arrival time of the echo. The function f(t) may be the shape of the echo measured on a reference sample having known physical characteristics or determined by simulation. The echo time, or times, as determined are then used to yield film thicknesses or interface characteristics.

In view of the foregoing descriptions, it should thus be realized that the teaching of this invention also pertains to methods for deducing the physical characteristics of thin films or interfaces, in which the steps include the sequential application of some or all of the above-described methods in order to determine the physical parameters of a complex sample having more than one layer or interface.

The teaching of this invention also pertains to methods for deducing the sound velocity and refractive index of a film or substrate in which a stress wave is generated by a light pulse, and in which an oscillating response is observed in the detected probe beam as a function of delay, and measurements of the oscillation period are made corresponding to at least two angles of incidence of the probe beam on the sample's surface. Measurements at several angles may be made sequentially or simultaneously. In this case the film may be partially absorbing, and could be a film which is underneath (i.e, on the substrate side of) another partially-absorbing film or films.

Also encompassed by the teachings of this invention are methods of relating the quality of a sample to another reference sample prepared under a particular set of conditions, by comparing the observed temporal response of the sample with that measured for the reference sample under similar conditions. The result of the comparison may or may not ascribe a cause for any observed differences to a specific physical or chemical property of either sample.

The quality is considered a factor which relates the similarity or dissimilarity of the optical responses of the several samples to the generation of a stress wave or pulse by the pump beam.

This invention also pertains to the application of the pump and/or probe beams at different spatial locations on the sample with the intention of characterizing an intervening part of sample. The intervening part of the sample may be, by example, an interface, a crack, or a material in which signals cannot be directly generated, but which is desired to characterize.

The teaching of this invention furthermore pertains to methods and apparatus for exciting modes of one or two dimensional patterned objects for the purpose of characterizing their shapes, layer thickness, adhesion, and structural integrity. This aspect of the invention may be considered as a generalization of the foregoing features and advantages, and is directed to samples which are not thin films of uniform thickness and which may be large compared to their thickness. For these samples the analysis preferably includes the calculation of the stress, strain, electric fields due to the pump and probe light pulses, etc., as a function of two or three spatial coordinates rather than only the distance from the surface of the sample. While the time-step method described above may not be applicable to solving this problem, because it is applicable to one dimension, other numerical simulation methods may be applied to perform the calculation of how the stress changes with time. Also, the previously described simulations employ optical transfer matrices to calculate the electric field distribution of the pump light and the change in optical reflectivity (or other changes in the characteristics) of the probe light. However, the optical transfer matrix method is not applicable to patterned structures because, again, it is essentially a one dimensional method. Thus, another more suitable numerical method is used instead.

The teaching of this invention also includes methods and apparatus for exciting stress pulses in one part of a thin film or multilayer in order to detect a change in another part of the thin film, such as a presence of a chemical reaction, intermixing, or alloying at one or more interfaces within the sample.

Relatedly, the teaching of this invention also encompasses the characterization of interfacial chemical reactions between two or more layers, or between a layer and interface, and the correlation of the acoustical and optical measurements with reactant species. This includes the characterization of the structural phase, and one or more of the thickness and sound velocity of the layers in the sample, including any new layers formed by the chemical reaction.

The teachings of this invention also pertain to the characterization of ion implant dose, energy, species, or any other ion implant parameters for an ion implant made through a film for the purpose of, by example, altering its adhesion to a substrate or an underlying layer. This characterization is carried out in accordance with any of the above-described techniques, in which the adhesion may be deduced from the temporal characteristics of the observed probe response, or by a simple comparison with a reference response for a sample prepared under like conditions.

Finally, this invention teaches a method for deducing the derivative of the index of refraction n or extinction coefficient κ of a material with respect to stress or strain by making measurements of the reflectivity change in the material caused by a stress pulse, of which a computable fraction has also been detected in a second material whose derivatives of index of refraction and extinction coefficient with respect to stress or strain are known or may be determined separately.

It should thus be apparent that while the invention has been particularly shown and described with respect to a number of embodiments thereof, the teachings of this invention are not to be construed to be limited to only these disclosed embodiments. That is, changes in form and details may be made to these disclosed embodiments without departing from the scope and spirit of the invention. The teaching of this invention should thus be afforded a scope that is commensurate with the scope of the claims which follow.

What is claimed is:

1. A non-destructive system for characterizing a sample, comprising:
   means for generating an optical pump pulse and for directing the pump pulse to an area of the surface of the sample;
   means for generating an optical probe pulse and for directing the probe pulse to a same or different area of the surface of the sample so as to arrive in time after the pump pulse;
   means for measuring at least one transient response of the structure to the pump pulse by detecting a change in a reflected or transmitted portion of the probe pulse; and
   means, coupled to said measurement means, for determining an electrical resistance of at least a portion of the sample in accordance with the measured transient response.

2. A method for operating a non-destructive system for characterizing a sample, comprising the steps of:
   generating an optical pump pulse and directing the pump pulse to an area of the surface of the sample;
   generating an optical probe pulse and directing the probe pulse to a same or different area of the surface of the sample so as to arrive in time after the pump pulse;
   measuring at least one transient response of the structure to the pump pulse by detecting a change in a characteristic of a reflected or transmitted portion of the probe pulse; and
   determining an electrical resistance of a portion of the sample in accordance with the measured transient response.

3. A non-destructive system for characterizing a sample, comprising:
   a first subsystem for generating an optical pump pulse and for directing the pump pulse to an area of the surface of the sample and for generating an optical probe pulse and for directing the probe pulse to a same or different area of the surface of the sample so as to arrive after the pump pulse;
   a second subsystem for measuring at least one transient response of the sample to the pump pulse by detecting at least one of $\Delta R(t)$, $\Delta T(t)$, $\Delta P(t)$, $\Delta\phi(t)$ and $\Delta\delta(t)$ in a portion the optical probe pulse after the probe pulse is incident on the sample; and
   a third subsystem for correlating the detected at least one of $\Delta R(t)$, $\Delta T(t)$, $\Delta P(t)$, $\Delta\phi(t)$ and $\Delta\delta(t)$ with a value of electrical resistance of the sample, where
   $\Delta R(t)$ is a change in intensity of a reflected portion of the probe pulse, $\Delta T(t)$ is a change in intensity of a transmitted portion of the probe pulse, $\Delta P(t)$ is a change in polarization of the probe pulse, $\Delta\phi(t)$ is a change in optical phase of the probe pulse and $\Delta\delta(t)$ is a change in an angle of reflection of the probe pulse.

4. A method for operating a non-destructive system for characterizing a sample, comprising the steps of:
   generating optical pump pulses and directing the pump pulses to an area of the surface of the sample;
   generating optical probe pulses and directing the probe pulses to a same or different area of the surface of the sample such that an individual one of the optical probe pulses impinges on the surface of the sample after an individual one of the optical pump pulses impinges on the surface of the sample;
   measuring at least one transient response of the sample to the optical pump pulses from at least one of $\Delta R(t)$, $\Delta T(t)$, $\Delta P(t)$, $\Delta\delta(t)$ and $\Delta\phi(t)$ in a portion the optical probe pulses after the probe pulses impinge on the sample; and
   determining a value of electrical resistance of the sample using at least one of $\Delta R(t)$, $\Delta T(t)$, $\Delta P(t)$, $\Delta\phi(t)$, and $\Delta\delta(t)$, where
   $\Delta R(t)$ is a change in intensity of a reflected portion of the probe pulses, $\Delta T(t)$ is a change in intensity of a transmitted portion of the probe pulses, $\Delta P(t)$ is a change in polarization of the probe pulses $\Delta\phi((t)$ is a change in optical phase of the probe pulses and $\Delta\delta(t)$ is a change in an angle of reflection of the probe pulses.

5. A method for operating a non-destructive system for characterizing a sample, comprising the steps of:
   generating optical pump pulses and directing the pump pulses to a surface of the sample;
   generating optical probe pulses and directing the probe pulses to the surface of the sample such that an individual one of the optical probe pulses impinges on the surface of the sample after an individual one of the optical pump pulses impinges on the surface of the sample;

measuring a transient response of the sample to the optical pump pulses from at least a change in optical phase Δφ in a reflected portion of the optical probe pulses;

adjusting a value of a thermal diffusivity component in a model of the sample so as to obtain a best agreement between a simulation and the actual measured transient response; and determining a value of electrical resistance of the sample based at least in part on the adjusted value of the thermal diffusivity component.

6. A method for operating a non-destructive system for characterizing a sample, comprising the steps of:

generating optical pump pulses and directing the pump pulses to a surface of the sample;

generating optical probe pulses and directing the probe pulses to the surface of the sample such that an individual one of the optical probe pulses impinges on the surface of the sample after an individual one of the optical pump pulses impinges on the surface of the sample;

measuring a transient response of the sample to the optical pump pulses from at least a change in optical phase Δφ in a reflected portion of the optical probe pulses;

adjusting a value of an electronic thermal diffusivity component in a model of the sample so as to obtain a best agreement between a simulation and the actual measured transient response; and determining a value of electrical resistance of the sample based at least in part on the adjusted value of the electronic diffusivity component.

7. A method for operating a non-destructive sample characterizing system for determining an electrical resistance of an electrically conductive film, comprising the steps of:

providing a sample comprised of an electrically conductive film;

generating optical pump pulses and directing the pump pulses to a surface of the film;

generating optical probe pulses and directing the probe pulses to the surface of the film such that an individual one of the optical probe pulses impinges on the surface of the film after an individual one of the optical pump pulses impinges on the surface of the film;

measuring a transient response of the film to the optical pump pulses in a reflected portion of the optical probe pulses;

adjusting a value of at least one of a thermal diffusivity component and an electronic diffusivity component in a model of the sample so as to obtain a best agreement between a simulation and the actual measured transient response; and determining a value of electrical resistance of the electrically conductive film based at least in part on adjusted values of one or both of the thermal diffusivity component and the electronic diffusivity component.

* * * * *

UNITED STATES PATENT AND TRADEMARK OFFICE
CERTIFICATE OF CORRECTION

PATENT NO. : 6,208,421 B1  
DATED : March 27, 2001  
INVENTOR(S) : Humphrey J. Maris and Robert J. Stoner It is certified that error appears in the above-identified patent and that said Letters Patent is hereby corrected as shown below:

Claim 4,
Line 45, reverse "$\Delta\delta(t)$ and $\Delta\varphi(t)$" so that it reads -- $\Delta\varphi(t)$ and $\Delta\delta(t)$ --.

Signed and Sealed this

Twenty-fifth Day of September, 2001

Attest:

NICHOLAS P. GODICI  
*Attesting Officer*  *Acting Director of the United States Patent and Trademark Office*